US006020450A

United States Patent [19]
Matsuda et al.

[11] Patent Number: 6,020,450
[45] Date of Patent: Feb. 1, 2000

[54] ROOM TEMPERATURE CURABLE FLUOROPOLYMER COMPOSITION; AND FLUORINE-CONTAINING ORGANOSILICON COMPOUNDS, A METHOD OF PRODUCING THE SAME, AND ROOM TEMPERATURE CURABLE SILICONE COMPOSITION CONTAINING THE SAME

[75] Inventors: Takashi Matsuda; Takafumi Sakamoto; Shinichi Sato, all of Annaka; Noriyuki Koike, Yoshii-machi; Yasuo Tarumi, Takasaki; Tsuneo Kimura, Annaka; Yasushi Yamamoto, Takasaki; Masatoshi Arai, Annaka, all of Japan

[73] Assignee: Shin-Etsu Chemical Co., Ltd., Tokyo, Japan

[21] Appl. No.: 09/204,156

[22] Filed: Dec. 3, 1998

Related U.S. Application Data

[62] Division of application No. 08/934,085, Sep. 19, 1997, Pat. No. 5,919,886, which is a division of application No. 08/654,637, May 29, 1996, Pat. No. 5,705,591.

[30]     Foreign Application Priority Data

| May 29, 1995 | [JP] | Japan | 7-182038 |
| Sep. 14, 1995 | [JP] | Japan | 7-262088 |
| Sep. 14, 1995 | [JP] | Japan | 7-262106 |
| Sep. 14, 1995 | [JP] | Japan | 7-262316 |

[51] Int. Cl.$^7$ .................................................. C08G 77/24
[52] U.S. Cl. ................................ 528/42; 528/34; 528/14; 528/17; 528/21; 528/22
[58] Field of Search ..................... 528/42, 34, 14, 528/17, 21, 22

[56]     References Cited

U.S. PATENT DOCUMENTS

| 3,895,043 | 7/1975 | Wagner et al. |
| 3,950,588 | 4/1976 | McDougal |
| 4,100,136 | 7/1978 | Carter et al. |
| 5,208,312 | 5/1993 | Boutevin et al. |
| 5,300,613 | 4/1994 | Kishita et al. |
| 5,314,981 | 5/1994 | Takago et al. ............................ 528/36 |
| 5,352,752 | 10/1994 | Koike et al. |
| 5,380,811 | 1/1995 | Kishita et al. |
| 5,416,183 | 5/1995 | Sato et al. |
| 5,605,958 | 2/1997 | Yoneda et al. .......................... 524/755 |
| 5,705,586 | 1/1998 | Sato et al. |
| 5,705,591 | 1/1998 | Matsuda et al. |

*Primary Examiner*—David W. Wu
*Assistant Examiner*—Caixia Lu-Ruh
*Attorney, Agent, or Firm*—Oblon, Spivak, McClelland, Maier & Neustadt, P.C.

[57]     ABSTRACT

A room temperature curable fluoropolymer composition is provided which comprises (A) a straight chain fluoropolymer compound containing, in its backbone chain, at least one structure selected from a perfluoroalkylene structure and a perfluoropolyether structure and having a hydrolyzable silyl group at both ends of its molecular chain, (B) an organic compound having at least one carbonyl group per molecule, and (C) one compound selected from (C-1) an organic compound having at least one primary amino group per molecule and (C-2) a compound having at least one proton per molecule and having an acid dissociation constant (pKa) in water of 2 or less. Another room temperature curable composition is also provided which comprises said (A) component, (B') an organosilicon compound having at least two silanol groups per molecule, and (C') a condensation accelerator. These compositions are not only excellent in heat resistance, weatherability, electrical properties, processability, chemical resistance, solvent resistance and oil repellant properties, but also excellent in fast curability and deep-portion curability. A novel compound which is suitable as said fluoropolymer compound (A) is further provided.

14 Claims, No Drawings

ROOM TEMPERATURE CURABLE FLUOROPOLYMER COMPOSITION; AND FLUORINE-CONTAINING ORGANOSILICON COMPOUNDS, A METHOD OF PRODUCING THE SAME, AND ROOM TEMPERATURE CURABLE SILICONE COMPOSITION CONTAINING THE SAME

This application is a divisional application of Ser. No. 08/934,085, filed on Sep. 19, 1997, now U.S. Pat. No. 5,919,886, which is a divisional application of Ser. No. 08/654,637, filed on May 29, 1996, now U.S. Pat. No. 5,705,591.

BACKGROUND OF THE INVENTION

1. Field of the Invention

The present invention relates to a condensation curable type room temperature curable fluoropolymer composition, particularly a composition excellent in fast curability and deep-portion curability; and to fluorine-containing organosilicon compounds suitable for obtaining elastomers useful in, for example, rubber materials and release agents, a method of producing said organosilicon compounds; and room temperature curable silicone compositions containing the same compounds.

2. Description of the Background

Conventionally, as a condensation curable type room temperature curable composition, there are known those containing, as a base component, a polymer, the backbone chain of which consists of organosiloxane structures or polyoxyalkylene structures and which has a crosslinking point at both ends of the molecular chain. Since these compositions are liquid prior to curing, they are excellent in processability. Further, the resulting cured product is excellent in heat resistance, weatherability, electrical properties, processability and the like, so that it is employed in various fields. However, since the cured product is inferior in chemical resistance, solvent resistance and oil repellant properties, its uses are limited.

While, room temperature curable fluoropolymer compositions comprising, as a main component, a fluoropolymer, the backbone chain of which consists of fluorine-containing polymer structures, having a hydrolyzable group at both ends of the molecular chain; a crosslinking agent; and optionally a catalyst is described in, for example, Japanese Patent Publication (Kokoku) No. 63-61336, U.S. Pat. No. 3,950,588 and EP 0151877. The curing of these compositions proceeds as the hydrolyzable group at the ends of said fluoropolymer and the crosslinking agent undergo dehydration condensation by water present in the atmosphere to be cured. The room temperature curable fluoropolymer compositions are not only excellent in processability prior to curing and cured products obtained by curing the same are excellent in heat resistance, weatherability and electrical properties, but also are superior in chemical resistance, solvent resistance and oil repellant properties.

However, these conventional room temperature curable fluoropolymer compositions are slow in curing rate, and especially it requires a long time for curing the deep portions thereof when left to stand in the atmosphere, compared to curable compositions comprising, as a main component, a polymer of which backbone chain consists of organopolysiloxane or polyoxyalkylene. For example, it requires a time of 1 to 2 weeks for curing from the surface to 5 mm in depth of said curable fluoropolymer composition at room temperature in the atmosphere. That is, these compositions have the defects of being extremely poor in fast curability and deep-portion curability. This is because the water content in the atmosphere is hardly to permeate into the fluoropolymer.

On the other hand, organofluoro compounds are employed in various fields. For example, elastomers obtained by crosslinking the organofluoro compounds at a high temperature of 150° C. or more with a crosslinking agent are used as rubber materials and release agents. Although most of elastomers obtained from the conventional organofluoro compounds are unsatisfactory in chemical resistance, especially solvent resistance, resistance to acids and resistance to bases. Further, although elastomers to be used in, for example, sealants and molded products are desirable to be excellent in said chemical resistance and otherwise in releasability and water repellant properties, and to cure at room temperature, organofluoro compounds capable of producing such elastomers have not hitherto been known.

SUMMARY OF THE INVENTION

Accordingly, a first object of the present invention is to provide a room temperature curable fluoropolymer composition excellent in fast curability and deep-portion curability.

A second object of the present invention is to provide a novel fluorine-containing organosilicon compound suitable for obtaining elastomers excellent in chemical resistance, releasability and water repellant properties, a method of producing the same, and a room temperature curable silicone resin composition containing the same.

The first object of the present invention is accomplished by providing a room temperature curable silicone resin composition containing, as essential components, either the following three components (A), (B) and (C), or the following three components (A), (B') and (C').

A first aspect of the present invention is a room temperature curable fluoropolymer composition (sometimes, referred to as first room temperature curable fluoropolymer composition) comprising:

(A) a straight chain fluoropolymer compound containing, in its backbone chain, at least one structure selected from the group consisting of a perfluoroalkylene structure and a perfluoropolyether structure and having a hydrolyzable silyl group at both ends of its molecular chain;

(B) an organic compound having at least one carbonyl group per molecule; and (C) one compound selected from the group consisting of (C-1) an organic compound having at least one primary amino group per molecule and (C-2) a compound having at least one proton per molecule and having an acid dissociation constant (pKa) in water of 2 or less.

A second aspect of the present invention is a room temperature curable fluoropolymer composition (sometimes, referred to as second room temperature curable fluoropolymer composition) comprising:

(A) a straight chain fluoropolymer compound containing, in its backbone chain, at least one structure selected from the group consisting of a perfluoroalkylene structure and a perfluoropolyether structure and having a hydrolyzable silyl group at both ends of its molecular chain;

(B') an organosilicon compound having at least two silanol groups per molecule; and (C') a condensation accelerator.

The present invention also provides a cured product obtained by curing said first or second composition.

The second object of the present invention is accomplished by providing a novel fluorine-containing organosilicon compound, a method of producing the same, and a room temperature curable silicone composition containing the same.

A third aspect of the present invention is a fluorine-containing organosilicon compound represented by the following general formula (8):

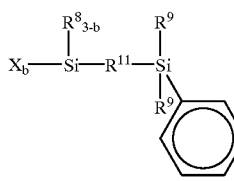

wherein $R^8$ and $R^9$ are independently a substituted or unsubstituted monovalent hydrocarbon group; $R^{10}$ is independently a hydrogen atom or a substituted or unsubstituted monovalent hydrocarbon group; $R^{11}$ is independently a substituted or unsubstituted divalent hydrocarbon group; Rf is independently a divalent perfluoroalkylene group or a divalent perfluoropolyether group; X is independently a hydrolyzable group; Q is a group represented by the following general formula (9):

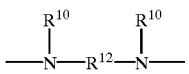

wherein $R^{12}$ is a substituted or unsubstituted divalent hydrocarbon group which may have at least one atom selected from the group consisting of an oxygen atom, a nitrogen atom and a silicon atom within the backbone, and $R^{10}$ is as defined above, or a group represented by the following general formula (10):

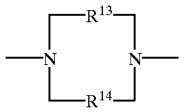

wherein $R^{13}$ and $R^{14}$ are independently a substituted or unsubstituted divalent hydrocarbon group; a is an integer of 0 or more; and b is 1, 2 or 3.

A forth aspect of the present invention is a method of producing said fluorine-containing organosilicon compound comprising reacting an organosilicon compound represented by the following general formula (11):

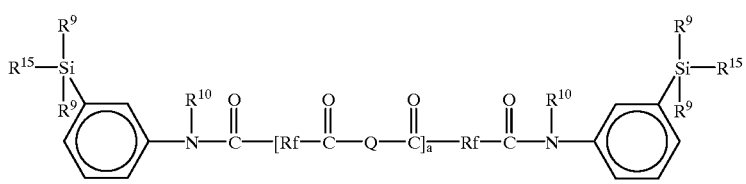

wherein $R^9$, $R^{10}$, Rf, Q and a are as defined above, $R^{15}$ is independently a substituted or unsubstituted monovalent hydrocarbon group having an aliphatic unsaturated bond capable of undergoing hydrosilylation reaction with a hydrogen atom bonded to a silicon atom, and an organohydrogensilane represented by the following general formula (12):

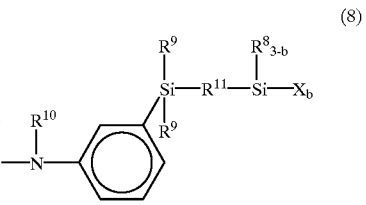

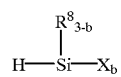

wherein $R^8$, b and X are as defined above, in the presence of a hydrosilylation catalyst.

A fifth aspect of the present invention is a room temperature curable silicone composition containing said fluorine-containing organosilicon compound.

The present invention also provides a cured product obtained by curing said room temperature curable silicone composition.

The room temperature curable fluoropolymer composition of the present invention is not only excellent in heat resistance, weatherability, electrical properties, processability, chemical resistance, solvent resistance and oil repellant properties, but also excellent in fast curability and deep-portion curability in which conventional compositions of this type are poor. Therefore, a cured product obtained by curing the composition of the invention is useful as, for example, oil sealants for motor vehicles, sealing materials for chemical apparatus, and electrical and electronic sealing materials and potting materials.

The fluorine-containing organosilicon compound of the present invention has hydrolyzable silyl groups at the ends, so that, for example, it is crosslinked by reacting with moisture (water content) in the air, whereby an elastomer can be produced. Further, since the fluorine-containing organosilicon compound of the present invention has a high fluorine content, a room temperature curable silicone compound containing the same can produce, for example, sealants, molded products, extruded products, covering materials and release agents which are excellent not only in solvent resistance and chemical resistance but also in releasability and water repellant properties.

DETAILED DESCRIPTION OF THE PREFERRED EMBODIMENTS

The present invention will be now described in more detail. Incidentally, in the following description, Me means a methyl group, and Ph means a phenyl group.

[First Room Temperature Curable Fluoropolymer Compositions]

(A) Straight Chain Fluoropolymer Compounds

The straight chain fluoropolymer compound of component (A) [hereinafter, referred to as fluoropolymer (A)] is a main component of the fluoropolymer composition.

Preferable fluoropolymer (A) includes one exemplified by the following general formula (1):

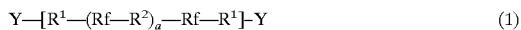
$$Y\text{---}[R^1\text{---}(Rf\text{---}R^2)_a\text{---}Rf\text{---}R^1]\text{---}Y \quad (1)$$

wherein Rf is a divalent group selected from the group consisting of a perfluoroalkylene group, a divalent perfluoropolyether group and a combination of the perfluoroalkylene group with the divalent perfluoropolyether group, $R^1$ and $R^2$, which may be the same or different, are each a substituted or unsubstituted divalent hydrocarbon group which may contain at least one atom selected from the group consisting of oxygen, nitrogen and silicon atoms, a is an integer of 0 or more, and Y is a hydrolyzable silyl group.

In the general formula (1), the perfluoroalkylene group represented by Rf includes, for example, a straight chain or branched chain perfluoroalkylane group represented by the following formula (2):

$$\text{---}C_pF_{2p}\text{---} \quad (2)$$

wherein p is an integer of 1 to 10, preferably 1 to 6.

The divalent perfluoropolyether group represented by Rf includes one represented by the general formula (3):

$$\text{---}(Rf'\text{---}O)_q\text{---} \quad (3)$$

wherein a plurality of Rf', which may be the same or different, are a straight chain or branched chain perfluoroalkylene group having 1 to 6 carbon atoms, preferably 1 to 3 carbon atoms, q is an integer of 1 to 500, preferably 2 to 400, more preferably 10 to 200.

In the general formula (3), examples of the structural unit represented by the formula —(Rf'—O)—include —$CF_2O$—, —$CF_2CF_2O$—, —$CF_2CF_2CF_2O$—, —$CF(CF_3)CF_2O$—, —$CF_2CF_2CF_2CF_2O$—, —$CF_2CF_2CF_2CF_2CF_2CF_2O$—and —$C(CF_3)_2O$—. Among them, particularly preferred are —$CF_2O$—, —$CF_2CF_2O$—, —$CF_2CF_2CF_2O$— and —$CF(CF_3)CF_2O$—.

Specific examples of Rf include:
—$C_4F_8$—; —$C_6F_{12}$—;
—[$CF(CF_3)OCF_2$]$_3$[$CF_2OCF(CF_3)$]$_2$—;
—[$CF(CF_3)OCF_2$]$_{15}$[$CF_2OCF(CF_3)$]$_{15}$—;
—[$CF(CF_3)OCF_2$]$_m$[$CF_2OCF(CF_3)$]$_n$—
wherein n and m are an integer such that n+m is 38 on average;
—$CF_2CF_2OFC_2(CF_2)_2CF_2OCF_2CF_2$—;
—$CF_2CF_2OCF_2CF$ ($CF_3$) $OCF_2(CF_2)_2CF_2O$—CF ($CF_3$) $CF_2OCF_2$—;
—$CF_2(OCF_2CF_2)_n(OCF_2)_mOCF_2$—wherein n is an integer of 5 to 50 on average, and m is an integer of 1 to 10 on average;
—$CF(CF_3)$ [$OCF(CF_3)CF_2$]$_n$($OCF_2$)$_m$O—$CF(CF_3)$—
wherein n is an integer of 5 to 50 on average, and m is an integer of 1 to 10 on average;
—$CF_2CF_2(OCF_2CF_2CF_2)_nOCF_2CF_2$—wherein n is an integer of 5 to 100 on average;
—[$CF(CF_3)OCF_2$]$_n$[$CF_2OCF(CF_3)$]$_m$—wherein n and m are an integer such that n+m is an integer of 2 to 200 on average, preferably 30 to 110 on average; and
—[$CF(CF_3)OCF_2$]$_n$($CF_2$)$_2$[$CF_2OCF(CF_3)$]$_m$—wherein n and m are an integer such that n+m is an integer of 20 to 110 on average.

In the general formula (1), $R^1$ and $R^2$ include preferably a substituted or unsubstituted divalent hydrocarbon group having 1 to 20 carbon atoms, particularly one having 2 to 10 carbon atoms. Specific examples thereof include an alkylene group such as methylene, ethylene, propylene, methylethylene, butylene and hexamethylene groups; a cycloalkylene group such as a cyclohexylene group; an arylene group such as phenylene, tolylene, xylylene, naphthylene and biphenylene groups; a substituted group obtained by substituting part or the whole of hydrogen atoms contained in said groups with a halogen atom; and a combination of the substituted or unsubstituted alkylene group with the arylene group.

$R^1$ and $R^2$ may contain, in its structure, at least one atom selected from the group consisting of oxygen, nitrogen and silicon atoms. In this case, an oxygen atom, a nitrogen atom and a silicon atom each can be present in the hydrocarbon group or the end thereof as —O— or =C=O bonds; —NR'— bond wherein R' is a hydrogen atom, an aryl group or an alkyl group having 1 to 8 carbon atoms, particularly 1 to 6 carbon atoms; or a straight chain or cyclic organosiloxy group and organosilylene group as follows:

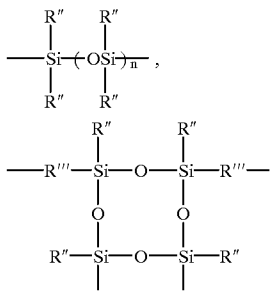

and

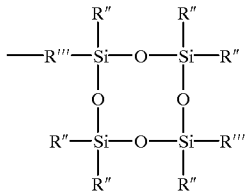

wherein R" is a substituted or unsubstituted monovalent hydrocarbon group having 1 to 8 carbon atoms, R'" is an arylene group or an alkylene group having 1 to 6 carbon atoms, and n is an integer of 0 to 10, preferably 0 to 5.

R" as mentioned above includes an alkyl group such as methyl, ethyl, propyl, isopropyl, butyl, isobutyl, tert-butyl, pentyl, neopentyl, hexyl, heptyl, octyl, nonyl and decyl groups; a cycloalkyl group such as cyclopentyl, cyclohexyl and cycloheptyl groups; an alkenyl group such as vinyl, allyl, propenyl, isopropenyl, butenyl, isobutenyl, hexenyl and cyclohexenyl groups; an aryl group such as phenyl, tolyl, xylyl and naphthyl groups; an aralkyl group such as benzyl, phenylethyl and phenylpropyl groups; and a substituted group obtained by substituting part or the whole of the hydrogen atoms of said groups with a halogen atom, such as chloromethyl, bromoethyl, chloropropyl and trifluoropropyl groups.

In the general formula (1), examples of $R^1$ and $R^2$ include the following groups:

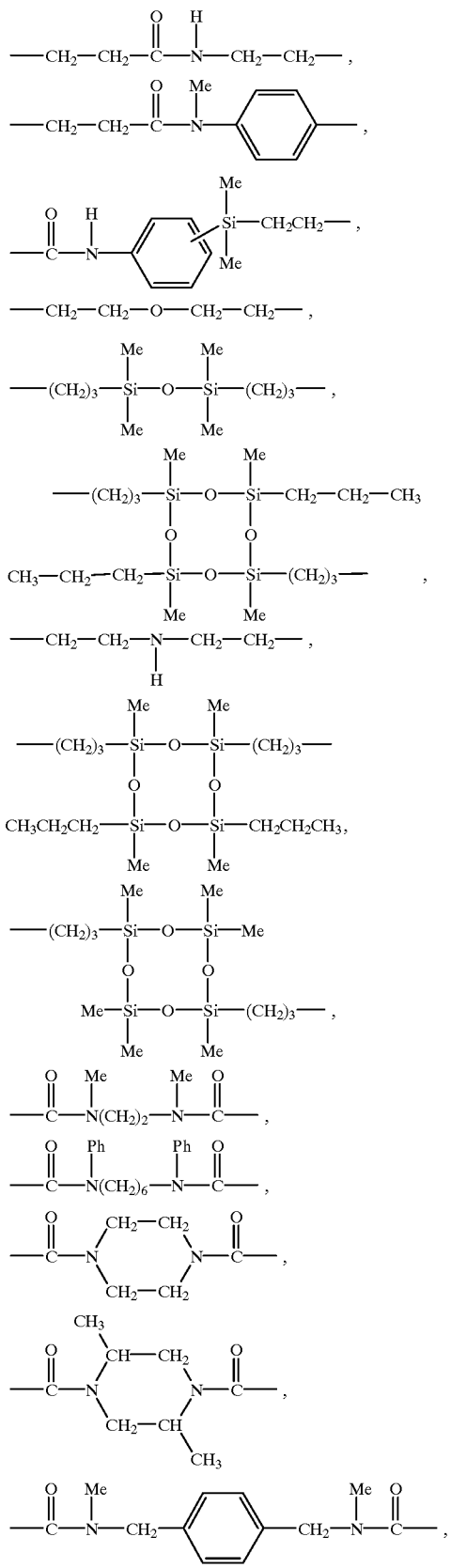

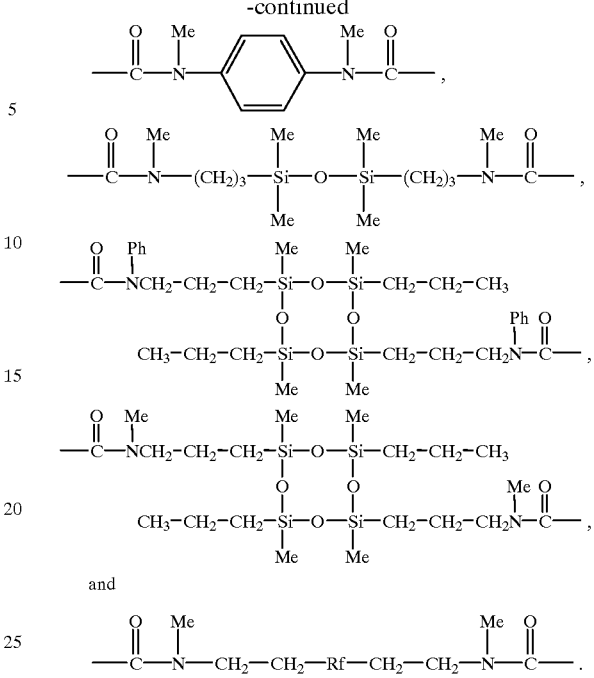

and

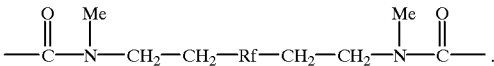

In the general formula (1), the range of a is preferably 0 to 10, more preferably 0 to 5.

The hydrolyzable silyl group present in both ends of fluoropolymer (A) includes, for example, one represented by the following general formula (4):

$$-SiR''_{3-b}X_b \qquad (4)$$

wherein X is a hydrolyzable group, R'' is a substituted or unsubstituted monovalent hydrocarbon group having 1 to 8 carbon atoms, and b is an integer of 1 to 3.

The hydrolyzable group (X) in the general formula (4) includes a carboxyl group, a ketoxime group, an alkoxy group, an alkenoxy group, an amino group, an aminoxy group, an amido group and a halogen atom such as fluorine, chlorine, bromine and iodine atoms.

The straight chain compound of component (A) may have a viscosity at 25° C. of generally 25 to 1,000,000 cSt, preferably 100 to 100,000 cSt. If the viscosity is too low, a cured product excellent in physical Properties may not be obtained. In contrast, if the viscosity is too high, the viscosity of the resulting composition may become high to thereby deteriorate workability when using the composition.

(B) Carbonyl Group-Containing Organic Compounds

The carbonyl group-containing organic compound [hereinafter, referred to as carbonyl compound (B)] of component (B) should have at least one carbonyl group per molecule.

The first room temperature curable composition of the present invention differs from the conventional condensation curable type room temperature curable fluoropolymer compositions. That is, the first composition not only supplies the water necessary for curing into the composition from the atmosphere but also supplies water therein either by the dehydration reaction of said component (B) with component (C-1) as mentioned later, which reaction is represented by the following reaction formula:

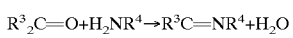

wherein $R^3$ and $R^4$ are an organic group, or by the dehydration reaction using, as a catalyst, component (C-2) as mentioned later, which reaction is represented by the following reaction formula:

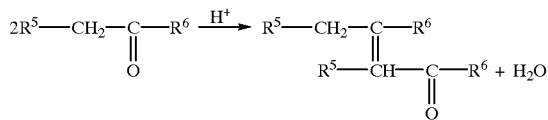

wherein $R^5$ and $R^6$ are a hydrogen atom or an organic group. Thus, since water is also produced in the deep portions of the composition, the composition can be fast cured even in said portions.

The carbonyl compound (B) includes, for example, ketones such as acetone, methyl ethyl ketone, acetophenone and acetylacetone; esters such as ethyl acetate, butyl acetate, methyl propionate, ethyl acrylate, butyrolactone and ethyl acetoacetate; amides such as dimethylformamide, diethylacetamide and butyrolactam; carboxylic acids such as acetic acid, propionic acid and benzoic acid; aldehydes such as acetaldehyde, n-butylaldehyde and benzaldehyde; silane coupling agents having a carbonyl group as a functional group; polymers and oligomers each having a carbonyl group; and a halogen-substituted compound in which part or the whole of hydrogen atoms contained in the above compounds has been substituted with a halogen atom.

Incidentally, considering steric hindrance when the carbonyl compound (B) is reacted with an amino compound (C-1) as described later, the carbon atom at a-position of the carbonyl compound (B) is preferred to be primary, secondary or part of an aromatic ring. If said carbon atom is tertiary, a desired effect may not be obtained because of the steric hindrance. Also, considering reactivity when the carbonyl compound (B) and a proton-carrying compound (C-2) as described later are subjected to dehydration condensation reaction, one of the carbon atoms adjacent to the carbonyl group of the carbonyl compound (B) is preferred to be a primary carbon atom. If all the adjacent carbon atoms are a secondary carbon atom, a tertiary carbon atom or part of an aromatic ring, the reactivity may be lowered and a desired effect may not be obtained.

Consequently, preferable examples of the carbonyl compound (B) include acetone, methyl ethyl ketone, methyl isobutyl ketone, 2-pentanone, 3-pentanone, 2-hexanone, 2-heptanone, acetophenone, cyclohexanone, acetylacetone, ethyl acetoacetate, acetaldehyde, n-butylaldehyde, benzaldehyde, hexachloroacetone and perfluoro-3-pentanone, and particularly, acetone, methyl ethyl ketone, 2-pentanone, cyclohexanone, ethyl acetoacetate, acetylacetone, hexachloroacetone and perfluoro-3-pentanone.

The carbonyl compound (B) is not limited to one of these organic compounds, and two or more thereof can be used.

Suitable amount of the carbonyl compound (B) is such that the carbonyl group contained therein is present in an amount of 0.001 to 0.5 mol, preferably 0.01 to 0.2 mol, per 100 g of the fluoropolymer (A). If the amount of the carbonyl group is too small, the deep-portion curability may not be exhibited. While, if the amount is too large, physical properties, after cured, such as rubber strength and elasticity may not be sufficiently obtained as intended.

(C-1) Amino Group-Containing Organic Compounds

The amino group-containing organic compound [hereinafter, referred to as amino compound (C-1)] should have at least one amino group per molecule. The amino compound (C-1) includes, for example, amines such as methylamine, ethylamine, butylamine, ethylenediamine and aniline; amino group-containing silane coupling agents such as γ-aminopropyltriethoxysilane; and polymers and oligomers each having an amino group.

As aforementioned, considering steric hindrance when the amino compound (C-1) and the carbonyl compound (B) are reacted, the carbon atom at a-position of the amino group of the amino compound (C-1) is preferred to be primary, secondary or part of an aromatic ring. If said carbon atom is tertiary, a desired effect may not be obtained due to the steric hindrance. Thus, preferable amino compound (C-1) includes, for example, ethylamine, butylamine, cyclohexylamine, ethylenediamine, hexamethylenediamine, benzylamine, aniline, polyvinylamine, polyallylamine, α-aminopropyltriethoxysilane and γ-aminopropylmethylpolysiloxane.

The amino compound (C-1) is not limited to one of these organic compounds, and two or more thereof can be used.

Suitable amount of the amino compound (C-1) is such that the amino group contained therein is present in an amount of 0.001 to 0.5 mol, preferably 0.01 to 0.2 mol per 100 g of the fluoropolymer compound (A). If the amount of the amino group is too small, the deep-portion curability may not be sufficiently exhibited. While, if the amount is too large, intended physical properties, after cured, such as rubber strength and elasticity may not be sufficiently obtained.

(C-2) Proton-Carrying Compounds

The proton-carrying compound of component (C-2) acts as a catalyst for the condensation reaction of the carbonyl compound (B) and should have at least one proton per molecule and further should be a compound having an acid dissociation constant (pKa) of 2 or less [the compound of this component being referred to as catalyst (C-2)]. If the compound has a pKa of more than 2, the acidity, that is, a dissociation degree of a proton is small and does not act effectively on the condensation reaction of the carbonyl compound (B).

The catalyst (C-2) includes, for example, carboxylic acids such as maleic acid, 5-aminosalicylic acid, 2,4-dinitrobenzoic acid, nitroacetic acid and oxalic acid; phenylalcohols such as picric acid; a halogen-substituted carboxylic acid in which part or the whole of the hydrogen atoms on the carbon atoms at a-position to the carbonyl group has been substituted with a halogen atom, such as dichloroacetic acid, trichloroacetic acid, difluoroacetic acid, trifluoroacetic acid and pentafluorobutyric acid; hydrogen halides such as hydrogen chloride, hydrogen bromide and hydrogen iodide; and oxoacids such as sulfurous acid, sulfuric acid, nitric acid, hypochlorous acid, perchloric acid, periodic acid, permanganic acid, p-toluenesulfonic acid, fluorosulfuric acid and trifluoromethanesulfonic acid.

Among them, those modified with fluorine are preferred since the modified compounds are excellent in compatibility with the fluoropolymer (A).

Since hydrogen halides and oxoacids are dangerous in handling, the other carboxylic acids are rather preferred.

Thus, most preferred is a halogen-substituted carboxylic acid in which part or the whole of the carbon atoms at α-position to the carbonyl group has been substituted with a halogen atom, such as difluoroacetic acid, trifluoroacetic acid and pentafluorobutyric acid.

The catalyst (C-2) is not limited to one of these organic or inorganic compounds, and two or more thereof can be used.

The amount of the catalyst (C-2) is preferably 0.0001 to 0.2 mol, and more preferably 0.001 to 0.1 mol, per 100 g of the fluoropolymer compound (A). If the amount of the catalyst (C-2) is too small, the deep-portion curability may not be sufficiently exhibited. While, if the amount is too large, intended physical properties, after cured, such as rubber strength and elasticity may not be sufficiently obtained.

Other Compounding Additives

In order to control the physical properties and the like of a cured product, various compounding additives can be added to the first room temperature curable composition of the present invention. Examples of them include condensation catalysts such as organotin esters, organotitanic acid esters and tetramethylguanidylpropyltrimethoxysilane; storage stabilizers such as methyltrimethoxysilane, methyltripropenoxysilane, vinyltributanoximesilane and methyltriacetoxysilane; reinforcing agents such as fumed silica, precipitated silica, titanium dioxide, aluminum oxide, silica powder, carbon powder, talc and bentonite; fibrous fillers such as asbestos, glass fiber and organic fiber; colorants such as pigments and dyes; heat-resistance improvers such as red oxide and cerium oxide; cold-resistance improvers; dehydrating agents; anti-corrosive agents; liquid reinforcing agents such as network polysiloxane comprised of triorganosiloxy units and $SiO_2$ units; and adhesion improvers such as γ-glycidoxypropyltriethoxysilane.

Preparation of the First Room Temperature Curable Composition

In the case of preparing the first room temperature curable composition of the present invention as one-pack type, the composition can be obtained by uniformly mixing said components (A), (B) and (C) and, if necessary, other compounding additives in a dry atmosphere. Also, in order to store the composition in the state of prior to curing, the carbonyl compound (B) or the amino compound (C) can be micro-encapsulated.

In the case of preparing said composition as two-pack type, for example, a liquid containing part of the fluoropolymer (A) and the carbonyl compound (B) and a liquid containing the remainder of the fluoropolymer (A) and the amino compound (C) are separately packed to obtain two packs, and two kinds of liquids contained in the packs are mixed when using the composition as a cured product. The two-pack type composition can also supply at a volume ratio of 1:1 therefrom by, for example, after separately packing said two kinds of liquids in an equal volume in a twin cartridge, pushing the resulting two-pack type liquids through a nozzle provided with a mixer while mixing the same liquids. Therefore, the two pack type composition has the effect of an easy working.

In this case, the temperature when mixing is preferably in the range of from room temperature to 60° C.

[Second room temperature curable fluoropolymer composition]

(A) Straight Chain Fluoropolymer Compounds

The straight chain fluoropolymer compound (A) used in the second room temperature curable fluoropolymer composition is the same as in the first room temperature curable fluoropolymer composition.

(B') Silanol Groups-Containing Organosilicon Compounds

The second room temperature curable composition of the present invention differs from the conventional condensation curable type room temperature curable fluoropolymer compositions. That is, the following reaction proceeds in the second composition, simultaneously with a crosslinking reaction effected by water to be supplied from the atmosphere.

That is, the condensation reaction between the fluoropolymer (A) and the silanol groups-containing organosilicon compound [hereinafter, referred to as silanol compound (B')] occurs as represented by the following reaction formula (5):

≡SiX+HOSi≡ → ≡SiOSi≡+HX　　(5)

wherein X is a hydrolyzable group, to form crosslinking. Thus, the second composition can be fast cured even in the deep portions.

The silanol compound (B') can be used as long as it has at least two silanol groups per molecule and the reaction of the reaction formula (5) occurs. For example, as a compound having a silanol group at both ends of the molecular chain, there can be enumerated a compound represented by the general formula (6):

(6)

wherein c is an integer of 1 or more, preferably 1 to 200, and R" is as defined above, and a compound represented by the general formula (7):

(7)

wherein $R^7$ is a substituted or unsubstituted divalent hydrocarbon group having 1 to 20, particularly 2 to 10, carbon atoms, and c and R" are as defined above. The above compounds can be singly or in a combination of two or more thereof.

In the general formula (7), specific examples of $R^7$ include an alkylene group such as methylene, ethylene, propylene, methylethylene, butylene and hexamethylene groups; a cycloalkylene group such as a cyclohexylene group; an arylene group such as phenylene, tolylene, xylylene, naphthylene and biphenylene groups; a substituted group obtained by substituting part or the whole of hydrogen atoms contained in said groups with a halogen atom and the like; and a combination of said substituted or unsubstituted alkylene group with said substituted or unsubstituted arylene group. Among them, preferred are methylene, ethylene, propylene, butylene, hexamethylene, cyclohexylene and phenylene groups, particularly ethylene, propylene, butylene and phenylene groups.

As a compound having silanol groups in the molecule, there can be enumerated a resinous compound constituted by bonding one unit or a combination of more units selected from $R''_3SiO_{1/2}$, $R''_2SiO$, $R''SiO_{3/2}$ and $SiO_2$ units to the silanol groups. The above constituting units may be directly bonded one another or may be bonded through a di- or more-valent hydrocarbon group.

The amount of the silanol compound (B') is not limited as long as the amount is such a range that physical properties required for a cured product of the composition are not damaged and is an amount sufficient to react with the hydrolyzable silyl group of the fluoropolymer (A). The silanol compound (B') is used in an amount of preferably 0.01 to 200 parts by weight, more preferably 1 to 100 parts by weight, per 100 parts by weight of the fluoropolymer (A). If the amount of the silanol compound (B') is too small, the deep-portion curability may not be sufficiently exhibited. While, if the amount is too large, intended physical properties such as chemical resistance, solvent resistance and oil repellant properties may not be obtained.

(C') Condensation Accelerators

The condensation accelerator of component (C') [hereinafter, referred to as condensation accelerator (C')] has an action accelerating the condensation reaction of the fluoropolymer (A) with the silanol compound (B'). As the accelerating agent, there can be used known agents as a catalyst for accelerating the condensation reaction of a hydrolyzable silyl group with a silanol group. These accelerating agents include, for example, metal salts and amine salts of organic carboxylic acids, such as lead 2-ethyloctoate, dibutyltin diacetate, dibutyltin dilaurate, butyltin tri-2-ethylhexoate, iron 2-ethylhexoate, cobalt 2-ethylhexoate, manganese 2-ethylhexoate, zinc 2-ethylhexoate, titanous caprylate, tin naphthenate, tin oleate, tin butylate, titanium naphthenate, zinc naphthenate, cobalt naphthenate, zinc stearate, ammonium trifluoroacetate and trifluoroacetic acid-diethylamine salt; organic acids such as p-toluenesulfonic acid, trifluoroacetic acid, trichloroacetic acid and picric acid; organotitanic acid esters, such as tetrabutyl titanate, tetra-2-ethylhexyl titanate, triethanolamine titanate, tetra(isopropenyloxy) titanate; orgaonotitanium compounds such as organosiloxytitanium and β-carbonyltitanium; alkoxyaluminum compounds; aminoalkyl group-substituted alkoxysilanes such as 3-aminopropyltriethoxysilane and N-(trimethoxysilylpropyl)ethylenediamine; amine compounds and salts thereof, such as hexylamine and dodecylamine phosphate; quaternary ammonium salts such as benzyltriethylamnmonium acetate; alkali metal salts of lower aliphatic acids, such as potassium acetate, sodium acetate and lithium oxalate; dialkylhydroxylamines such as dimethylhydroxylamine and diethylhydroxylamine; and guanidyl-containing compounds such as tetramethylquanidine, and quadinyl group-containing silanes and siloxanes, for example, the compounds represented by the following formulas:

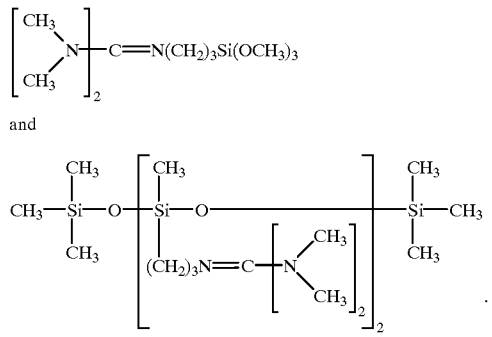

and

Among them, tin compounds, titanium compounds, organic acids and guanidyl-containing compounds are preferred, and guanidyl compounds are more preferred in view of fast curing the composition and improving the adhesive properties of the resulting cured product. They can be used singly or in a combination of two or more thereof.

The amount of the condensation accelerator (C') is generally 0.01 to 5 parts by weight, preferably 0.05 to 2 parts by weight, per 100 parts by weight of the total amount of the fluoropolymer (A) and the silanol compound (B').

Other Compounding Additives

In order to control the physical properties and the like of a cured product, various compounding additives can be added to the second room temperature curable composition of the present invention. Examples of them include storage stabilizers such as methyltrimethoxysilane, methyltripropenoxysilane, vinyltributanoximesilane and methyltriacetoxysilane; reinforcing agents such as fumed silica, precipitated silica, titanium dioxide, aluminum oxide, silica powder, carbon powder, talc and bentonite; fibrous fillers such as asbestos, glass fiber and organic fiber; colorants such as pigments and dyes; heat-resistance improvers such as red oxide and cerium oxide; cold-resistance improvers; dehydrating agents; anti-corrosive agents; adhesion improvers such as β-(3,4-epoxycyclohexyl)ethyltrimethoxysilane, γ-glycidoxypropyltriethoxysilane, γ-methacryloxypropyltrimethoxysilane, γ-methacryloxypropylmethyldiethoxysilane, N-β-(aminoethyl)-γ-aminopropyltrimethoxysilane, γ-aminopropyltriethoxysilane, γ-chloropropyltrimethoxysilane, γ-mercaptopropyltrimethoxysilane and γ-isocyanatopropyltriethoxysilane; and liquid reinforcing agents such as network polysiloxane comprised of triorganosiloxy units and $SiO_2$ units.

Preparation of the Second Room Temperature Curable Composition

In the case of preparing the second room temperature curable composition of the present invention as one-pack type, the composition can be obtained by uniformly mixing said components (A), (B') and (C') and, if necessary, other compounding additives in a dry atmosphere.

In the case of preparing said composition as two-pack type, for example, a liquid containing the fluoropolymer (A) and the condensation accelerator (C') and a liquid containing the silanol compound (B') are separately packed to obtain two packs and said two kinds of liquids contained in the packs are mixed when using the composition as a cured product. The two-pack type composition can also supply at a volume ratio of 1:1 therefrom by, for example, after separately packing said two kinds of liquids in an equal volume in a twin cartridge, pushing the resulting two-pack type liquids through a nozzle provided with a mixer while mixing the same liquids. Therefore, the two pack type composition has the effect of an easy working.

In this case, the temperature when mixing is preferably in the range of from room temperature to 60° C.

[Fluorine-Containing Organosilicon Compounds, a method of producing the same, and room temperature curable silicone compositions containing the same compound]

Fluorine-Containing Organosilicon Compounds

The fluorine-containing organosilicon compound of the present invention is represented by said general formula (8) and is a novel compound included in said component (A).

[1] Substituents $R^8$, $R^9$, $R^{10}$ and $R^{11}$ in the general formula (8):

In the general formula (8), the unsubstituted monovalent hydrocarbon group represented by $R^8$ and $R^9$ includes, for example, alkyl, cycloalkyl, aryl, aralkyl, alkenyl, acryloyloxypropyl and methacryloyloxypropyl groups. Said alkyl group includes, for example, an alkyl group having 1 to 10 carbon atoms, such as methyl, ethyl, propyl, isopropyl, butyl, isobutyl, tert-butyl, pentyl, neopentyl, hexyl, heptyl, octyl, nonyl and decyl groups; and typically a lower alkyl group having 1 to 3 carbon atoms, such as methyl, ethyl and propyl groups, and butyl, tert-butyl, hexyl and octyl groups.

Said cycloalkyl group includes, for example, a cycloalkyl group having 3 to 8 carbon atoms, such as cyclopentyl, cyclohexyl and cycloheptyl groups; and typically a cycloalkyl group having 5 to 6 carbon atoms, such as cyclopentyl and cyclohexyl groups.

Said aryl group includes, for example, an aryl group having 6 to 15 carbon atoms, such as phenyl, tolyl, xylyl, naphthyl and biphenylyl groups; and typically an aryl group having 6 to 8 carbon atoms, such as phenyl, tolyl and xylyl groups.

Said aralkyl group includes, for example, an aralkyl group having 7 to 10 carbon atoms, such as benzyl, phenylethyl, phenylpropyl and methylbenzyl groups; and typically an aralkyl group having 7 to 8 carbon atoms, such as benzyl and phenylethyl groups.

Said alkenyl group includes, for example, an alkenyl group having 2 to 10 carbon atoms, such as vinyl, allyl, propenyl, isopropenyl, butenyl, isobutenyl, hexenyl and cyclohexenyl; and typically an alkenyl group having 2 to 4 carbon atoms, such as vinyl, allyl and butenyl groups.

In the general formula (8), the substituted monovalent hydrocarbon group represented by said $R^8$ and $R^9$ includes a halogen-substituted group obtained by substituting at least part of the hydrogen atoms of said unsubstituted monovalent hydrocarbon group with a halogen atom such as fluorine, chlorine, bromine and iodine atoms; typically a halogen-substituted alkyl group having 1 to 8 carbon atoms, such as chloromethyl, 2-bromoethyl, 3-chloropropyl, 3,3,3-trifluoropropyl and 3,3,4,4,5,5,6,6,6-nonafluorohexyl groups; and more typically a halogen-substituted alkyl group having 3 to 8 carbon atoms, such as 3,3,3-trifluoropropyl and 3,3,4,4,5,5,6,6,6-nonafluorohexyl groups.

In the general formula (8), $R^{10}$ is a hydrogen atom or a substituted or unsubstituted monovalent hydrocarbon group. The substituted or unsubstituted monovalent hydrocarbon group of $R^{10}$ includes the same groups as exemplified for said $R^8$ and $R^9$.

In the general formula (8), the substituted or unsubstituted divalent hydrocarbon group of $R^{11}$ includes, for example, a divalent hydrocarbon group having 1 to 20, particularly 2 to 10, carbon atoms; typically an alkylene group such as methylene, ethylene, propylene, methylethylene, butylene and hexamethylene groups, and more typically an alkylene group having 1 to 3 carbon atoms such as methylene, ethylene and propylene; a cycloalkylene group having 3 to 6 carbon atoms such as a cyclohexylene group; an arylene group such as phenylene, tolylene, xylylene, naphthylene and biphenylene groups, and more typically an arylene group having 6 to 8 carbon atoms such as phenylene and tolylene groups; a substituted group obtained by substituting part or the whole of hydrogen atoms contained in said groups with a halogen atom and the like; and a combination of said substituted or unsubstituted alkylene group with said substituted or unsubstituted arylene group. Among them, preferred are ethylene and propylene in view of easy synthesis, stability of the resulting compound and the like.

[2] The substituent Q in the General Formula (8)

In the general formula (8), Q is a group represented by said general formula (9) or said general formula (10).

(i) The group represented by the general formula (9):

In the general formula (9), $R^{10}$ is as defined above.

In the general formula (9), $R^{12}$ includes said substituted or unsubstituted divalent hydrocarbon group as exemplified for $R^{11}$ and further a substituted or unsubstituted divalent hydrocarbon group containing at least one atom selected from the group consisting of an oxygen atom, a nitrogen atom and a silicon atom within the backbone exclusive of both the terminal ends of the divalent hydrocarbon group $R^{12}$. The oxygen atom in the divalent hydrocarbon of $R^{12}$ can be present as —O—, and the nitrogen atom can be present as —$NR^{16}$— wherein $R^{16}$ is a hydrogen atom, an alkyl group or an aryl group.

The alkyl group of $R^{16}$ includes, for example, methyl, ethyl, propyl, isopropyl, butyl, isobutyl, tert-butyl, pentyl, neopentyl, hexyl, heptyl and octyl groups, and particularly typically an alkyl group having 1 to 6 carbon atoms, such as methyl, ethyl, propyl, isopropyl, butyl, isobutyl, tert-butyl, pentyl, neopentyl and hexyl groups.

The aryl group of $R^{16}$ includes, for example, an aryl group having 6 to 8 carbon atoms such as phenyl, tolyl and xylyl groups.

The silicon atom in the divalent hydrocarbon group of $R^{12}$ can be present as a group containing a straight chain or cyclic organosiloxane or organosilylene group within the backbone of $R^{12}$, for example, as follows:

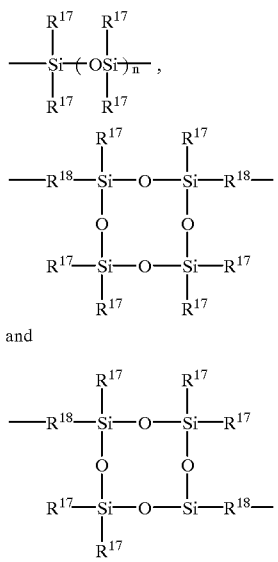

and wherein in said formulas $R^{17}$ is independently an alkyl group or an aryl group, $R^{18}$ is independently an alkylene group or an arylene group, and n is an integer of 0 to 10, typically 0 to 5.

The alkyl or aryl group of $R^{17}$ includes the same groups as exemplified for $R^{16}$. The alkylene group of $R^{18}$ includes, for example, an alkylene group having 1 to 10 carbon atoms, such as methylene, ethylene, propylene, butylene, pentylene, hexylene, heptylene, octylene, nonylene and decylene groups. The arylene group of $R^{18}$ includes, for example, an arylene group having 6 to 10 carbon atoms, such as phenylene, tolylene, xylylene and naphthylene.

Specific examples of the substituted or unsubstituted divalent hydrocarbon group having at least one atom selected from the group consisting of an oxygen atom, a nitrogen atom and a silicon atom within the backbone of $R^{12}$ include those represented by the following formulas:

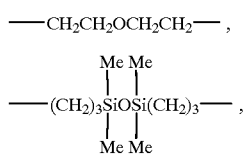

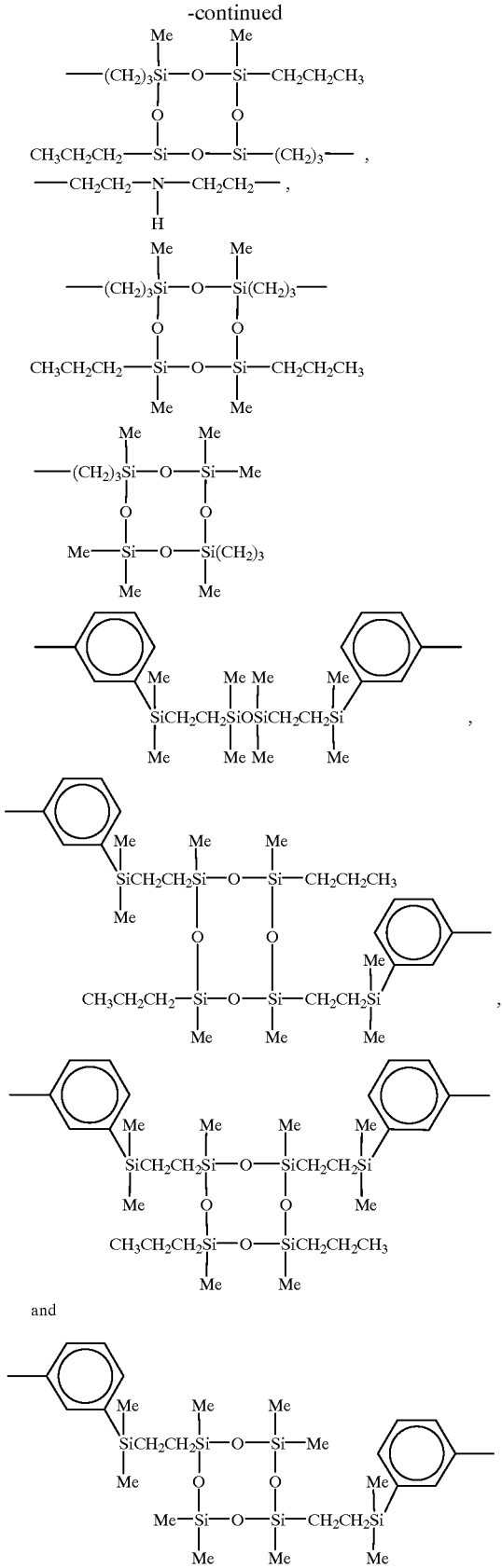

wherein in said formulas Me stands for a methyl group.

(ii) The group represented by the general formula (10):

In the general formula (10), the substituted or unsubstituted divalent hydrocarbon group of $R^{13}$ and $R^{14}$ includes the same groups as exemplified for $R^{11}$ in said general formula (8), typically an alkylene group such as methylene, ethylene, propylene, methylethylene, butylene and hexamethylene groups, and more typically an alkylene group having 1 to 3 carbon atoms such as methylene, ethylene and propylene; and a substituted compound obtained by substituting part or the whole of the hydrogen atoms of said groups with a halogen atom and the like.

(iii) Specific examples of the group represented by Q:

Specific examples of the group Q represented by the general formula (9) or the general formula (10) include those represented by the following formulas:

wherein in said formulas Me stands for a methyl group, Ph stands for a phenyl group, and Rf is a perfluoroalkylene group or a divalent perfluoropolyether group.

Rf in said formulas includes the same groups as exemplified for Rf in the general formula (8).

[3] The Substituent Rf in the General Formula (8)

The perfluoroalkylene group represented by Rf in the general formula (8) includes a straight chain or branched chain perfluoroalkylene group represented by the following general formula:

$$—C_mF_{2m}—$$

wherein m is an integer of 1 to 10, preferably 1 to 6.

The divalent perfluoropolyether group represented by Rf in the general formula (8) includes, for example, a group represented by the following formula:

$$—(\underset{Z}{CFOCF_2})_p—(CF_2)_r—(\underset{Z}{CFOCF})_q—$$

wherein Z is independently a fluorine atom or a trifluoromethyl group, p, q and r are an integer satisfying $p \geq 1$, $q \geq 1$ and $2 \leq p+q \leq 200$, preferably an integer satisfying $3 \leq p+q \leq 110$ and $0 \leq r \leq 6$; a group represented by the following general formula:

$$—CF_2CF_2OCF_2—(\underset{CF_3}{CFOCF_2})_s(CF_2)_r—(CF_2O\underset{CF_3}{CF})_t—CF_2OCF_2CF_2—$$

wherein r is as defined above, s and t are an integer satisfying $s \geq 0$, $t \geq 0$ and $2 \leq s+t \leq 200$, preferably an integer satisfying $3 \leq s+t \leq 110$; a group represented by the following general formula:

$$—\underset{Z}{CF}—(O\underset{Z}{CFCF_2})_u—(OCF_2)_v—O\underset{Z}{CF}—$$

wherein Z is as defined above, u and v are an integer satisfying $1 \leq u \leq 100$ and $1 \leq v \leq 100$; and a group represented by the following general formula:

$$—CF_2CF_2—(—OCF_2CF_2CF_2—)_w—OCF_2CF_2—$$

wherein w is an integer satisfying $1 \leq w \leq 100$.

Specific examples of such Rf include:

$$—C_4F_8—;$$

$$—C_6F_{12}—;$$

$$—(\underset{CF_3}{CFOCF_2})_3(CF_2O\underset{CF_3}{CF})_2—;$$

$$—(\underset{CF_3}{CFOCF_2})_{15}(CF_2O\underset{CF_3}{CF})_{15}—;$$

$$—(\underset{CF_3}{CFOCF_2})_m(CF_2O\underset{CF_3}{CF})_n—;$$

wherein n and m are an integer such that n+m is 38 on average;

$$—CF_2CF_2OCF_2(CF_2)_2CF_2—OCF_2CF_2—;$$

$$—CF_2CF_2OCF_2\underset{CF_3}{CFOCF_2}(CF_2)_2CF_2OC\underset{CF_3}{F}CF_2OCF_2CF_2—;$$

$$—CF_2(OCF_2CF_2)_n(OCF_2)_mOCF_2—$$

wherein n is an integer of 5 to 50 on average, for example, 8, and m is an integer of 1 to 10 on average, for example, 2;

$$—\underset{CF_3}{CF}(O\underset{CF_3}{CFCF_2})_n(OCF_2)_mO\underset{CF_3}{CF}—$$

wherein n is an integer of 5 to 50 on average, for example, 15, and m is an integer of 1 to 10 on average, for example, 2;

$$—CF_2CF_2(OCF_2CF_2CF_2)_nOCF_2CF_2—$$

wherein n is an integer of 5 to 100, for example, 10;

$$—(\underset{CF_3}{CFOCF_2})_n(CF_2O\underset{CF_3}{CF})_m—$$

wherein n and m are an integer such that n+m is 2 to 200, preferably 30 to 110, on average; and $$—(\underset{CF_3}{CFOCF_2})_n(CF_2)_2(CF_2O\underset{CF_3}{CF})_m—$$

wherein n and m are an integer such that n+m is 20 to 110, for example 30, on average.

[4] The Substituent X in the General Formula (8)

In the general formula (8), the hydrolyzable group represented by X includes, for example, a halogen atom such as a fluorine atom, a chlorine atom, a bromine atom and an iodine atom; and groups represented by the following general formulas:

$$—OR^{19}, \quad —OC\underset{R^{19}}{\overset{O}{\diagup\!\!\!\diagdown}}, \quad —OC\underset{R^{20}}{\overset{CH—R^{19}}{\diagup\!\!\!\diagdown}},$$

$$—OC\underset{OR^{20}}{\overset{CH—R^{19}}{\diagup\!\!\!\diagdown}}, \quad —ON=C\underset{R^{20}}{\overset{R^{19}}{\diagup\!\!\!\diagdown}} \text{ and } —N\underset{R^{20}}{\overset{R^{19}}{\diagup\!\!\!\diagdown}}$$

wherein in said formulas $R^{19}$ and $R^{20}$ are independently a hydrogen atom or a substituted or unsubstituted monovalent hydrocarbon group.

The substituted or unsubstituted monovalent hydrocarbon group represented by said $R^{19}$ and $R^{20}$ includes, for example, an alkyl group such as methyl, ethyl, propyl, isopropyl, butyl and isobutyl groups, typically an alkyl group having 1 to 4 carbon atoms such as methyl, ethyl, propyl and isobutyl groups; a cycloalkyl group having 3 to 6 carbon atoms, such as a cyclohexyl group; an alkenyl group such as vinyl, allyl, propenyl, isopropenyl, butenyl and isobutenyl groups, typically an alkenyl group having 2 to 4 carbon atoms such as vinyl and isopropenyl groups; an aryl group such as a phenyl group; and a substituted group obtained by substituting part of the hydrogen atoms of said groups with an alkoxy group and the like, for example, an alkoxy-substituted alkyl group such as methoxymethyl, methoxyethyl, ethoxymethyl and ethoxyethyl groups.

[5] Other Definitions in the General Formula (8)

In the general formula (8), a is an integer of 0 or more, typically an integer of 0 to 10, and more typically 0, 1, 2, 3, 4, 5 or 6. Accordingly, the organofluoro compound of the general formula (8) contains at least one perfluoroalkylene group or at least one divalent perfluoropolyether group per molecule.

In the general formula (8), b is independently 1, 2 or 3. Therefore, the fluorine-containing organosilicon compound of the general formula (8) contains 1 to 3 hydrolyzable groups X per molecule.

[6] Fluorine-Containing Organosilicon Compounds

The fluorine-containing organosilicon compound represented by the general formula (8) includes from a polymer having a low viscosity of several ten cSt to a raw rubber-like solid polymer. For example, when using the organosilicon compound as a heat-curable rubber, it is advisable to use a raw rubber-like polymer in view of an easy handling. While, when using the organosilicon compound as a liquid rubber, it is advisable to use a polymer having a viscosity at 25° C. of about 100 to 100,000 cSt. If an organosilicon compound having an extremely low viscosity is used, the resulting cured product may not have elasticity and may be brittle.

Method of Producing the Fluorine-Containing Silicon Compound

The production method of the present invention is a method of producing the fluorine-containing silicon compound of said general formula (8) comprising reacting the organosilicon compound represented by said general formula (11) and the organohydrogensilane or organohydrogensiloxane represented by said general formula (12) in the presence of a hydrosilylating catalyst.

[1] The Organosilicon Compound of the General Formula (11)

In the general formula (11), $R^9$, $R^{10}$, Rf, Q and a are as defined above, and $R^{15}$ is independently a substituted or unsubstituted monovalent hydrocarbon group having an aliphatic unsaturated bond capable of hydrosilylation-reacting with a hydrogen atom bonded to a silicon atom.

Said $R^{15}$ includes, for example, an alkenyl group having 2 to 8, more typically 2 to 6, carbon atoms, such as vinyl, allyl, propenyl, isopropenyl, butenyl, hexenyl and cyclohexenyl groups.

[2] Production Method of the Organosilicon Compound having the General Formula (11)

(i) Production method of the organosilicon compound where a is 0:

The organosilicon compound [the following general formula (11-1)] where in the general formula (11), a is 0 is synthesized, for example, as shown in the following reaction formula, by reacting a compound having an acid fluoride group at both ends represented by the general formula (13) and an amine compound represented by the general formula (14) in the presence of an acid-scavenger such as triethylamine.

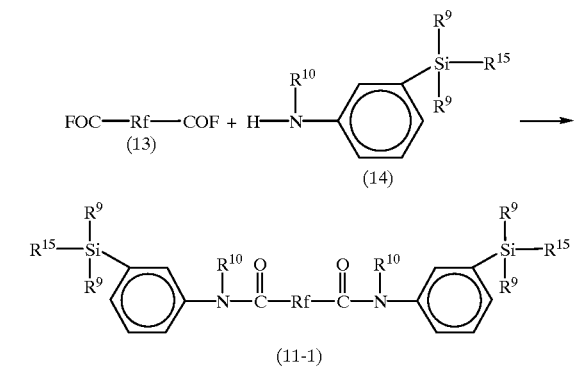

In the reaction formula, $R^9$, $R^{10}$, $R^{15}$ and Rf are as defined above.

The compounding ratio of the compound of the general formula (13) to the amine compound of the general formula (14) is not particularly limited, but preferably the amount (A) of the compound having the formula (13) used / the amount (B) of the compound having the formula (14) used is 0.5 to 0.2 in terms of molar ratio.

The reaction condition is not particularly limited and generally the reaction may be effected at 20 to 100° C. for 1 to 8 hours, preferably at 20 to 50° C. for 2 to 4 hours.

(ii) Production method of the organosilicon compound where a is 1 or more:

The organosilicon compound where in the general formula (11), a is 1 or more is synthesized, for example, by reacting the compound of the general formula (13) and a compound represented by the following general formula (15):

$$H—Q—H \qquad (15)$$

wherein Q is as defined above, in the presence of an acid-scavenger such as triethylamine and thereafter reacting the resulting reaction product with the amine compound represented by the general formula (14).

The compounding ratio of the general formula (13) and the compound of the general formula (15) is not particularly limited as long as the amount (A) of the compound having the formula (13) used is, in terms of molar ratio, not less than the amount(C) of the compound having the formula (15) used. The a in the general formula (8) can become an intended value by controlling the amount ratio (A)/(C). If the amount ratio (A)/(C) is large, a polymer having a relatively small molecular weight can be synthesized. While, if the value of the amount ratio (A)/(C) is brought near to 1, a polymer of a large molecular weight can be synthesized. The reaction condition may be the same as that of said (I).

In the organosilicon compounds of the above formula (11), the organosilicon compound where Q has a silicon atom within the backbone, can be synthesized by first synthesizing, in the case of $R^{15}$ of the amine compound having the formula (14) being a vinyl group, a compound having a vinyl group at both ends represented by the following general formula (16), and then reacting this compound with a compound represented by the following general formula (17) in the presence of the same addition reaction catalyst as above.

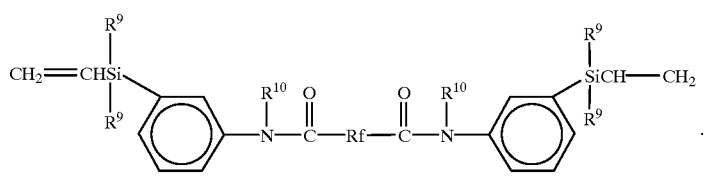

(16)

wherein $R^9$, $R^{10}$ and Rf are as defined above.

$$H-P-H \quad (17)$$

wherein P is, for example:

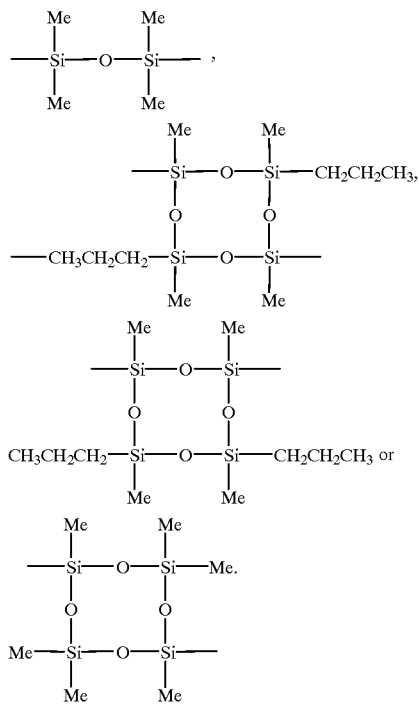

In this reaction, the ratio of the amount of the compound having a vinyl group at both ends represented by the above formula (16) used to the compound of the formula (17) used is not particularly limited as long as the amount (d) of the compound having the formula (16) used is not less than the amount (e) of the compound having the formula (17) in terms of molar ratio. Incidentally, if the amount ratio (d)/(e) is large, a polymer having a relatively small molecular weight can be synthesized, while if the value of the amount ratio (d)/(e) is brought near to 1, a polymer of a large molecular weight can be synthesized.

The reaction temperature may be about 50 to 150° C., preferably 80 to 120° C. The reaction time may be about 2 to 4 hours.

[3] The Compound of the General Formula (12) and the Catalyst

In the general formula, $R^8$, X and b are as defined above.

Said catalyst includes platinum family metal catalysts well known as a catalyst for use in hydrosilylation reaction, for example, chloroplatinic acid; alcohol-modified chloroplatinic acid (see U.S. Pat. No. 3,220,972); a complex of chloroplatinic acid with an olefin(see U.S. Pat. No. 3,159,601, U.S. Pat. No. 3,159,662 and U.S. Pat. No. 3,775,452); a catalyst comprising platinum black, palladium or the like supported on a carrier such as alumina, silica and carbon; rhodium-olefin complex; chlorotris(triphenylphosphine) rhodium (Wilkinson's catalyst). Among them, complex catalysts are preferably dissolved in an organic solvent such as an alcohol solvent, a ketone solvent and an ether solvent for use. The amount of the catalyst may be a so-called catalytic amount.

[4] Production of the Fluorine-Containing Silicon Compound

The fluorine-containing silicon compound of the present invention can be obtained by reacting the organosilicon compound of the general formula (11) with the compound of the general formula (12) in the presence of said catalyst. The amount of the compound having the general formula (12) used is generally 2 to 10 mols, preferably 2 to 5 mols, per mol of the organosilicon compound having the general formula (11).

The reaction temperature may be about 50 to 150° C., preferably 80 to 120° C. The reaction temperature may be about 2 to 4 hours. After the end of the reaction, the compound of the formula (12) remaining in the reaction products can be removed by vacuum-stripping.

The thus obtained organosilicon compound of the present invention has the hydrolyzable group X at both ends of the molecule, so that, for example, it is cohydrolyzed by the water content present in the atmosphere and simultaneously copolymerized to form a rubber-like cured product. Accordingly, the fluorine-containing organosilicon compound of the present invention can be used as a base polymer of room temperature curable silicone resin compositions.

Room Temperature Curable Silicone Compositions

The room temperature curable silicone composition (hereinafter, sometimes referred to as third room temperature curable composition) of the present invention contains a catalyst in addition to the fluorine-containing silicon compound of the general formula (8), and to the composition, an adhesive assistant can be added.

Said catalyst accelerates more the curing rate of the composition and includes, for example, metal salts of organic carboxylic acids, such as lead 2-ethyloctoate, dibutyltin diacetate, dibutyltin dilaurate, butyltin tri-2-ethylhexoate, iron 2-ethylhexoate, cobalt 2-ethylhexoate, manganese 2-ethylhexoate, zinc 2-ethylhexoate, titanous caprylate, tin naphthenate, tin oleate, tin butylate, titanium naphthenate, zinc naphthenate, cobalt naphthenate, zinc stearate; organotitanic acid esters, such as tetrabutyl titanate, tetra-2-ethylhexyl titanate, triethanolamine titanate, tetra (isopropenyloxy) titanate; organotitanium compounds such as organosiloxytitanium and β-carbonyltitanium; alkoxyaluminum compounds; amine compounds and salts thereof, for example, aminoalkyl group-substituted alkoxysilanes such as 3-aminopropyltriethoxysilane and N-(trimethoxysilylpropyl)ethylenediamine, hexylamine and dodecylamine phosphate; quaternary ammonium salts such as benzyltriethylammonium acetate; alkali metal salts of lower aliphatic acids, such as potassium acetate, sodium acetate and lithium oxalate; dialkylhydroxylamines such as dimethylhydroxylamine and diethylhydroxylamine; and guanidyl-containing compounds such as tetramethylguanidine and guanidyl group-containing silanes and siloxanes, for example, the compounds represented by the following formulas:

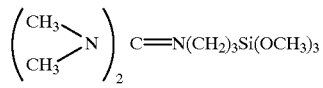

and

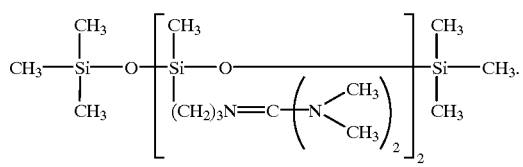

They can be used singly or in a combination of two or more thereof. Among them, guanidyl-containing compounds are preferred in view of favorably effecting the curing reaction and also having a function improving the adhesive properties.

Suitable amount of the catalyst is generally about 0.1 to 5 parts by weight per 100 parts by weight of the amount of the fluorine-containing organosilicon compound having the general formula (8) of the present invention.

Said adhesive assistant improves more the adhesive properties of a cured product obtained by curing the third composition to various substrates. Such adhesive assistants include, for example, vinylchlorosilane, vinyltrimethoxysilane, vinyltris(β-methoxyethoxy)silane, β-(3,4-epoxycyclohexyl) ethyltrimethoxysilane, γ-glycidoxypropyltriethoxysilane, γ-methacryloxypropyltrimethoxysilane, γ-methacryloxypropylmethyldiethoxysilane, N-β-(aminoethyl)-γ-aminopropyltrimethoxysilane, γ-aminopropyltriethoxysilane, γ-chloropropyltrimethoxysilane, γ-mercaptopropyltrimethoxysilane, γ-isocyanatopropyltriethoxysilane, and a partially fluorinated silane such as 3,3,3-trifluoropropyltrimethoxysilane and the compounds represented by the following formulas:

and

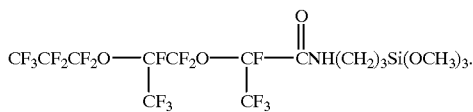

Further, in addition to said catalyst and adhesive assistant, various additives conventionally used for the compositions of this type in the art can be compounded in the third composition of the present invention and include, for example, reinforcing agents such as fumed silica, precipitated silica, titanium dioxide, aluminum oxide, silica powder, talc and bentonite; fibrous fillers such as asbestos, glass fiber and organic fiber; potassium methacrylate; colorants; red oxide; and cerium oxide. They may be added in a predetermined amount in accordance with the intended use.

If necessary, the third composition of the present invention can be stored or used as a solution in which the composition has been diluted with a non-aqueous organic solvent. Particularly, to use the composition as a solution in an organic solvent is suitable in forming a thin cured film. Such an organic solvent includes, for example, hydrocarbon solvents such as n-hexane, cyclohexane, toluene, petroleum ether and xylene; ether solvents such as diethyl ether, n-butyl ether, dioxane and tetrahydrofuran; ketone solvents such as acetone, methyl ethyl ketone, dibutyl ketone and ethyl acetate; chlorinated hydrocarbon solvents such as methylene chloride, chlorobenzene and chloroform; nitrile solvents such as acetonitrile; fluorine solvents such as trifluorobenzene and methaxylene hexafluoride; and alcohol solvents such as methanol, ethanol, isopropanol and n-butanol. If necessary, they may be used as a mixture of two or more thereof.

The third room temperature curable composition of the present invention can form a cured film excellent in, for example, adhesive properties to various substrates and strength in addition to the properties inherent in a fluorine-containing film, such as water repellant properties, oil repellant properties, chemical resistance and anti-contamination properties, by being cured at room temperature. Thus, the third composition of the present invention is useful as coatings or paints for use in construction field, industrial plants and various apparatus. Further, the third composition is excellent in adhesive properties to various metals, resins and concretes, so that upon coating on armoring materials, the beauty thereof can be maintained for a long period of time. Besides, the third composition of the present invention can be used as surface-treatments, for example, various powders such as silica filler, silica powder, ceramic powder, metal powder and sand to exhibit, for example, the effect of providing water repellant and oil repellant properties.

The third room temperature curable composition of the present invention can be obtained as a one-pack type room temperature curable silicone composition by uniformly mixing a predetermined amount of each of said components in a dry atmosphere. In this composition, hydrolysis and condensation polymerization reaction proceed by the moisture in the air to form a cured product consisting of a rubber elastomer. The third composition of the present invention is cured at room temperature, but the curing can be also accelerated by heating. The resulting cured product is excellent in any of characteristics such as solvent resistance, chemical resistance, heat resistance and cold resistance since the fluorine-containing organosilicon compound as a base component in the composition contains fluorine in an extremely high content.

This composition is suitable as sealings and coatings for use in building and construction industries and otherwise useful as adhesives and sealings for use in elecrical and electronic parts and as FIPG materials for use in motor vehicle industry.

EXAMPLES

The present invention will be now specifically described in the following, with reference to working examples thereof and comparative examples. In these examples, Me stands for a methyl group, and Ph stands for a phenyl group.

Example 1

Preparation of a First Room Temperature Curable Composition 100 g of a straight-chain compound having a viscosity of 34200 cSt at 25° C. blocked with a trimethoxysilyl group at both ends of the molecular chain, represented by the following formula:

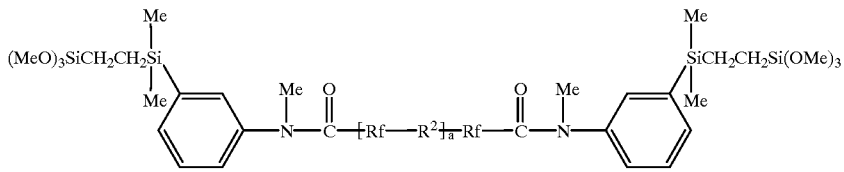

wherein a is 1 on average, Rf is a divalent group represented by the formula:

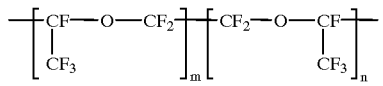

wherein m and n are an integer such that m+n is 38 on average, and $R^2$ is a divalent group represented by the formula:

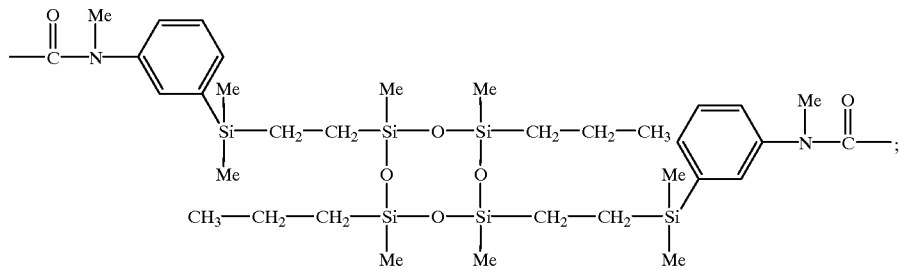

2.16 g of methyl ethyl ketone (0.03 mol in terms of a carbonyl group); 2.19 g of n-butylamine (0.03 mol in terms of an amino group); 0.2 g of dibutyltin dilaurate; 25 g of precipitated silica; 4 g of fumed silica; and 1 g of vinyltrimethoxysilane were mixed in an anhydrous state to prepare a first room temperature curable composition.

Test for Fast Curability

In order to test the fast-curability of the resulting composition, the composition was cast and formed into a mold having a depth of 2 mm. The resulting sheet was left to stand in an atmosphere of 20° C. and 50% RH for 24 hours. After the 24 hours, curing of the whole sheet was confirmed. Then, the rubber physical properties of the cured product were measured in accordance with JIS-K-6301. As a result, hardness was 55 (measured by a spring type hardness tester type A defined in JIS-A), elongation was 120%, and tensile strength was 28 Kgf/cm².

Test for Deep-Portion Curability

In order to test the deep-portion curability of the resulting composition, the composition was cast into a cylindrical tube made of glass having a diameter of 20 mm and a length of 100 mm. Then, the cylindrical tube was left to stand in an atmosphere of 20° C. and 50% RH for 24 hours. Upon breaking the cylindrical tube to take out the composition, the thickness of rubber-like portions produced by curing was 100 mm.

Comparative Example 1

A composition was prepared in the same manner as in Example 1, except that the methyl ethyl ketone and the n-butylamine were not used. Then, the composition was tested under the same condition as in Example 1. However, since the resulting composition was hardly cured to the form of a rubber, the rubber physical properties of a cured product thereof could not be measured.

Further, the resulting composition was cured in the cylindrical tube to measure the thickness of the rubber-like portions of the cured product. As a result, the thickness was 0.6 mm.

Example 2

100 g of a straight-chain compound having a viscosity of 32500 cSt at 25° C. blocked with a methyldiisopropenoxysilyl group at both ends of the molecular chain, represented by the following formula:

wherein a is 3 on average, Rf is a divalent group represented by the formula:

wherein m and n are an integer such that m+n is 38 on average, and $R^2$ is a divalent group represented by the formula:

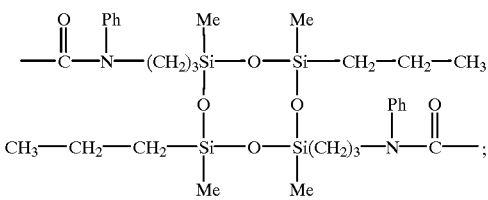

1.44 g of methyl ethyl ketone (0.02 mol in terms of a carbonyl group); 4.42 g of γ-aminopropyltriethoxysilane (0.02 mol in terms of an amino group); 0.2 g of dibutyltin dilaurate; 8 g of fumed silica; and 1 g of vinyltrimethoxysilane were mixed in an anhydrous state to prepare a first room temperature curable composition.

In order to test the fast curability of the resulting composition, the composition was tested under the same condition as in Example 1. Further, the rubber physical properties of the resulting cured product were measured in accordance with JIS-K-6301. The results are shown in Table 1.

Example 3

100 g of a straight-chain compound having a viscosity of 84,700 cSt at 25° C. blocked with a trimethoxysilyl group at both ends of the molecular chain, represented by the following formula:

1.96 g of cyclohexanone (0.02 mol in terms of a carbonyl group); 1.98 g of cyclohexylamine (0.02 mol in terms of an amino group); 0.5 g of dibutyltin dilaurate; 8 g of fumed silica; and 2 g of methyltri(methylethylketoxyimino)silane were mixed in an anhydrous state to prepare a first room temperature curable composition.

In order to test the fast curability of the resulting composition, the composition was tested under the same condition as in Example 1. Further, the rubber physical properties of the resulting cured product were measured in accordance with JIS-K-6301. The results are shown in Table 1.

Example 4

100 g of a straight-chain compound having a viscosity of 18,700 cSt at 25° C. blocked with a trimethoxysilyl group at both ends of the molecular chain, represented by the following formula:

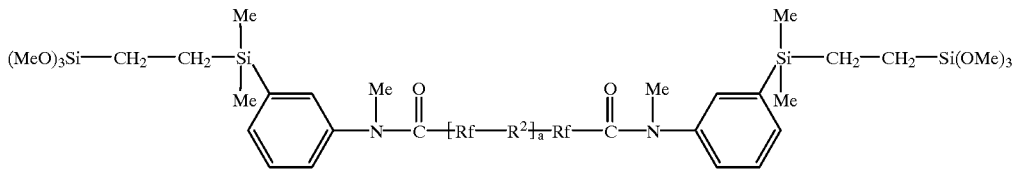

wherein a is 2 on average, Rf is a divalent group represented by the formula:

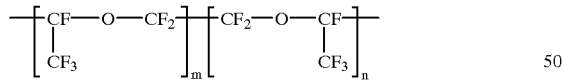

wherein m and n are an integer such that m + n is 38 on average, and $R^2$ is a divalent group represented by the formula:

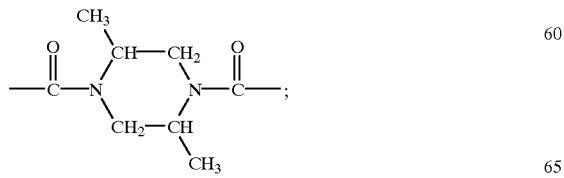

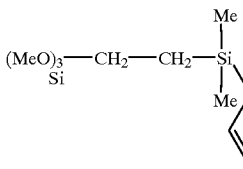 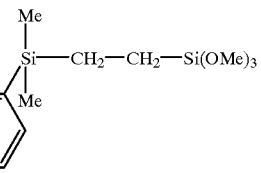

wherein Rf is a divalent group represented by the formula:

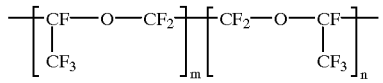

wherein m and n are an integer such that m+n is 94 on average; 2.45 g of cyclohexanone (0.025 mol in terms of a carbonyl group); 1.83 g of n-butylamine (0.025 mol in terms of an amino group); 0.2 g of dibutyltin dimethoxide; 50 g of colloidal calcium carbonate; and 1 g of vinylmethoxysilane were mixed in an anhydrous state to prepare a first room temperature curable composition.

In order to test the fast curability of the resulting composition, the composition was tested under the same condition as in Example 1. Further, the rubber physical properties of the resulting cured product were measured in accordance with JIS-K-6301. The results are shown in Table 1.

Example 5

100 g of a straight-chain compound having a viscosity of 24,200 cSt at 25° C. blocked with a trimethoxysilyl group at both ends of the molecular chain, represented by the following formula:

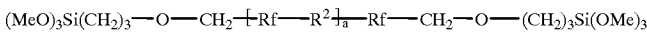

wherein a is 2 on average, and Rf is a divalent group represented by the formula:

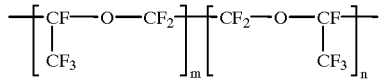

wherein m and n are an integer such that m+n is 38 on average and $R^2$ is a divalent group represented by

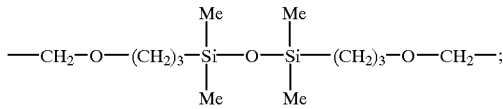

2.45 g of cyclohexanone (0.025 mol in terms of a carbonyl group); 1.83 g of n-butylamine (0.025 mol in terms of an amino group); 0.2 g of dibutyltin dimethoxide; 30 g of colloidal calcium carbonate; 6 g of fumed silica; and 1 g of vinylmethoxysilane were mixed in an anhydrous state to prepare a first room temperature curable composition.

In order to test the fast curability of the resulting composition, the composition was tested under the same condition as in Example 1. Further, the rubber physical properties of the resulting cured product were measured in accordance with JIS-K-6301. The results are shown in Table 1.

TABLE 1

|  | Rubber physical properties | | |
|---|---|---|---|
|  | Hardness (JIS-A) | Elongation (%) | Tensile strength (Kgf/cm$^2$) |
| Example 1 | 55 | 120 | 28 |
| Example 2 | 48 | 230 | 25 |
| Example 3 | 50 | 200 | 35 |
| Example 4 | 38 | 160 | 20 |
| Example 5 | 40 | 150 | 18 |
| Comparative Example 1 | Could not be measured. | Could not be measured. | Could not be measured. |

Example 6

Preparation of a First Room Temperature Curable Composition 100 g of the same straight-chain compound having a viscosity of 34,200 cSt at 25° C. blocked with a trimethoxysilyl group at both ends of the molecular chain, as used in Example 1; 5.88 g of cyclohexanone (0.06 mol); 0.68 g of trifluoroacetic acid (0.006 mol); 0.2 g of dibutyltin dilaurate; 25 g of precipitated silica; 4 g of fumed silica; and 1 g of vinyltrimethoxysilane were mixed in an anhydrous state to prepare a first room temperature curable composition.

Test for Fast Curability

In order to test the fast-curability of the resulting composition, the composition was cast and formed into a mold having a depth of 2 mm. The resulting sheet was left to stand in an atmosphere of 20° C. and 50% RH for 48 hours. After the 48 hours, curing of the whole sheet was confirmed. Then, the rubber physical properties of the cured product were measured in accordance with JIS-K-6301. As a result, hardness was 54 (measured by a spring type hardness tester type A defined in JIS-A), elongation was 140%, and tensile strength was 23 Kgf/cm$^2$.

Test for Deep-Portion Curability

In order to test the deep-portion curability of the resulting composition, the composition was cast into a cylindrical tube made of glass having a diameter of 20 mm and a length of 100 mm. Then, the cylindrical tube was left to stand in an atmosphere of 20° C. and 50% RH for 48 hours, upon breaking the cylindrical tube to take out the composition, the thickness of rubber-like portions produced by curing was 100 mm.

Comparative Example 2

The composition prepared in Comparative Example 1 was tested under the same condition as in Example 6. However, since the resulting composition was hardly cured in the test for fast-curability, the rubber physical properties of a cured product thereof could not be measured.

Further, in the test for deep-portion curability, the thickness of the resulting rubber-like cured portions was 0.6 mm.

Example 7

100 g of a straight-chain compound having a viscosity of 75,500 cSt at 25° C. blocked with a methyldiisopropenoxysilyl group at both ends of the molecular chain, represented by the following formula:

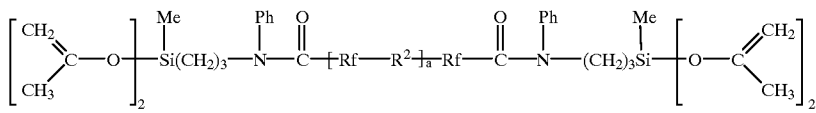

wherein a is 2 on average, Rf is a divalent group represented by the formula:

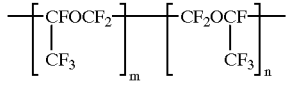

wherein m and n are an integer such that m+n is 38 on average, and $R^2$ is a divalent group represented by the formula:

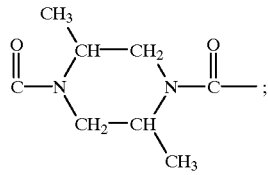

3.60 g of methyl ethyl ketone (0.05 mol); 1.72 g of p-toluenesulfonic acid (0.01 mol); 0.2 g of dibutyltin dilaurate; 8 g of fumed silica; and 1 g of vinyltrimethoxysilane were mixed in an anhydrous state to prepare a first room temperature curable composition.

The fast curability of the resulting composition was tested under the same condition as in Example 6. Further, the rubber physical properties of the resulting cured product were measured in accordance with JIS-K-6301. The results are shown in Table 2.

Example 8

100 g of a straight-chain compound having a viscosity of 27,300 cSt at 25° C. blocked with a methyldiacetoxysilyl group at both ends of the molecular chain, represented by the following formula:

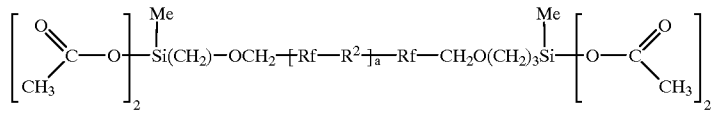

wherein a is 2 on average, Rf is a divalent group represented by the formula:

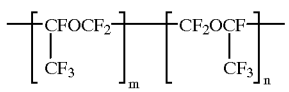

wherein m and n are an integer such that m+n is 38 on average, and $R^2$ is a divalent group represented by the formula:

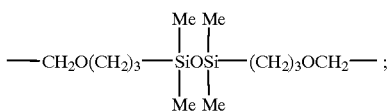

5.12 g of ethyl acetoacetate (0.04 mol); 3.30 g of a carboxylic acid (0.01 mol) represented by the formula: $CF_3CF_2CF_2OCF(CF_3)COOH$; 40 g of finely divided silica; and 1.5 g of methyltriacetoxysilane were mixed in an anhydrous state to prepare a first room temperature curable composition.

The fast curability of the resulting composition was tested under the same condition as in Example 6. Further, the rubber physical properties of the resulting cured product were measured in accordance with JIS-K-6301. The results are shown in Table 2.

Example 9

100 g of a straight-chain compound having a viscosity of 20,600 cSt at 25° C. blocked with a methyldiacetoxysilyl group at both ends of the molecular chain, represented by the following formula:

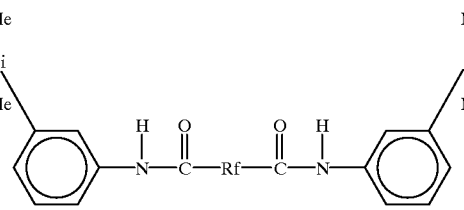

wherein Rf is a divalent group represented by the formula:

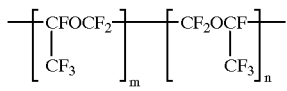

wherein m and n are an integer such that m+n is 94 on average; 4.90 g of cyclohexanone (0.05 mol); 3.30 g of a carboxylic acid (0.01 mol) represented by the formula: $CF_3CF_2CF_2OCF(CF_3)COOH$; 0.2 g of dibutyltin dimethoxide; 10 g of fumed silica; and 1.5 g of methyltriacetoxysilane were mixed in an anhydrous state to prepare a first room temperature curable composition.

The fast curability of the resulting composition was tested under the same condition as in Example 6. Further, the rubber physical properties of the resulting cured product were measured in accordance with JIS-K-6301. The results are shown in Table 2.

TABLE 2

| | Rubber physical properties | | |
|---|---|---|---|
| | Hardness (JIS-A) | Elongation (%) | Tensile strength (Kgf/cm$^2$) |
| Example 6 | 54 | 140 | 23 |
| Example 7 | 49 | 190 | 31 |
| Example 8 | 41 | 240 | 18 |
| Example 9 | 55 | 160 | 38 |
| Comparative Example 2 | Could not be measured. | Could not be measured. | Could not be measured. |

Example 10
Preparation of a Second Room Temperature Curable Composition 100 parts by weight of the same straight-chain compound having a viscosity of 34,200 cSt at 25° C. blocked with a trimethoxysilyl group at both ends of the molecular chain, as used in Example 1; 50 parts by weight of a dimethylpolysiloxane having a viscosity of 730 cSt at 25° C. blocked with a silanol group at both ends of the molecular chain; 3.3 parts by weight of a silanol compound represented by the formula: $HOSi(Me_2)OSi(Me_2)OH$; 0.2 part by weight of dibutyltin dilaurate; 25 parts by weight of precipitated silica; and 4 parts by weight of fumed silica were mixed in an anhydrous state to prepare a second room temperature curable composition.

Test for Fast Curability

In order to test the fast-curability of the resulting composition, the composition was tested under the same condition as in Example 1 and, as a result, curing of the whole sheet formed was confirmed. Then, the rubber physical properties of the cured product were measured in accordance with JIS-K-6301. As a result, hardness was 45 (measured by a spring type hardness tester type A), elongation was 190%, and tensile strength was 26 Kgf/cm$^2$.

Test for Deep-Portion Curability

In order to test the deep-portion curability of the resulting composition, the composition was tested under the same condition as in Example 1 and, as a result, the thickness of rubber-like portions produced by curing was 100 mm.

Comparative Example 3

A composition was prepared in the same manner as in Example 10, except that the dimethylpolysiloxane and the silanol compound were not used. Then, the composition was tested under the same condition as in Example 1.

However, since the resulting composition was hardly cured in the test for fast-curability, the rubber physical properties of a cured product thereof could not be measured.

Further, in the test for deep-portion curability, the thickness of the resulting rubber-like cured portions was 0.6 mm.

Example 11

100 parts by weight of the same straight-chain compound having a viscosity of 84700 cSt at 25° C. blocked with a trimethoxysilyl group at both ends of the molecular chain, as used in Example 3; 50 parts by weight of a dimethylpolysiloxane having a viscosity of 4,800 cSt at 25 ° C. blocked with a silanol group at both ends of the molecular chain; 25 parts by weight of an organopolysiloxane resin having an average compositional formula of $Me_{0.6}Si_{1.7}$ and having silanol groups in an amount of 0.09 mol/100 g; 0.5 part by weight of dibutyltin dioctate; and 10 parts by weight of fumed silica were mixed in an anhydrous state to prepare a second room temperature curable composition.

In order to test the fast curability of the resulting composition, the composition was tested under the same condition as in Example 1. Further, the rubber physical properties of the resulting cured product were measured in accordance with JIS-K-6301. The results are shown in Table 3.

Example 12

100 parts by weight of a straight-chain compound having a viscosity of 25300 cSt at 25° C. blocked with a methyldiacetoxysilyl group at both ends of the molecular chain, represented by the following formula:

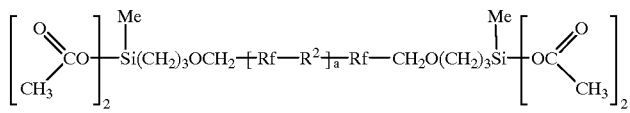

wherein a is 2 on average, Rf is a divalent represented by the formula:

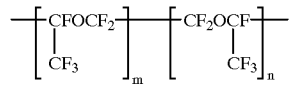

wherein m and n are an integer such that m+n is 38 on average, and $R^2$ is a divalent group represented by the formula:

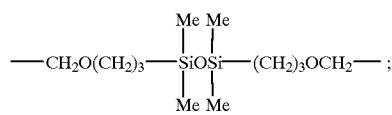

25 parts by weight of a dimethylpolysiloxane having the formula: $HO\text{—}[Si(Me_2)O]_p\text{—}H$ wherein p is 15 on average; 0.3 part by weight of dibutyltin dimethoxide; 50 parts by weight of finely divided silica; and 8 parts by weight of fumed silica were mixed in an anhydrous state to prepare a second room temperature curable composition.

In order to test the fast curability of the resulting composition, the composition was tested under the same condition as in Example 1. Further, the rubber physical properties of the resulting cured product were measured in accordance with JIS-K-6301. The results are shown in Table 3.

Example 13

100 parts by weight of the same straight-chain compound having a viscosity of 18,700 cSt at 25° C. blocked with a trimethoxysilyl group at both ends of the molecular chain, as used in Example 4; 35 parts by weight of a dimethylpolysiloxane having the formula: $HO\text{—}[Si(Me_2)O]_p\text{—}H$ wherein p is 15 on average; 4.3 parts by weight of diphenyldihydroxysilane; 1.0 part by weight of γ-aminopropyltriethoxysilane; 0.2 part by weight of dibutyltin dimethoxide; 10 parts by weight of fumed silica; and 1 part by weight of acetylene black carbon were mixed in an anhydrous state to prepare a second room temperature curable composition.

In order to test the fast curability of the resulting composition, the composition was tested under the same condition as in Example 1. Further, the rubber physical properties of the resulting cured product were measured in accordance with JIS-K-6301. The results are shown in Table 3.

TABLE 3

|  | Rubber physical properties | | |
|---|---|---|---|
|  | Hardness (JIS-A) | Elongation (%) | Tensile strength (Kgf/cm²) |
| Example 10 | 45 | 190 | 26 |
| Example 11 | 43 | 250 | 38 |
| Example 12 | 48 | 200 | 30 |
| Example 13 | 48 | 150 | 32 |
| Comparative Example 3 | Couid not be measured. | Couid not be measured. | Couid not be measured. |

Example 14

Production of a Starting Compound for a Fluorine-Containing Organosilicon Compound Into a 300 ml four-necked flask provided with a stirring rod, a thermometer, a Dimroth condenser and a dropping funnel, 189.2 g of a compound (viscosity at 25° C.: 430 cSt) having an acid fluoride group at both ends, represented by the following formula:

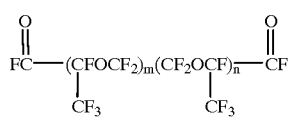

wherein m and n are an integer such that m+n is 38 on average was charged. While stirring at room temperature, a mixture of 13.8 g of a compound represented by the following formula:

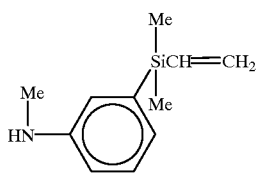

and 6.5 g of triethylamine was dropwise added thereto through the dropping tunnel. After the end of the addition, a reaction was effected at 60° C. for 2 hours. Then, the resulting reaction mixture was filtered under pressure, and the filtrate was stripped under a reduced pressure of 3 mmHg at 120° C. to obtain 195.3 g of a pale yellowish, transparent liquid compound. The liquid compound was charged into the same flask as above, 50.0 g of m-xylene hexafluoride was added therein, and the temperature was raised to 100° C. with stirring, followed by adding 0.2 g of a 2% isopropylalcohol solution of chloroplatinic acid. Thereto, 4.9 g of cyclotetrasiloxane represented by the formula:

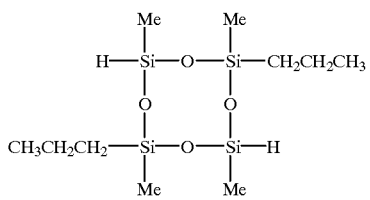

was dropwise added through the dropping funnel to effect a reaction. After the end of the addition, the reaction product was analyzed by gas chromatography while aging, and it was confirmed that the cyclotetrasiloxane had disappeared. Thereafter, the content of the flask was cooled to room temperature. Then, after 1.5 g of active carbon was charged into the flask and stirring was effected, the reaction mixture was filtered under pressure. The resulting filtrate was stripped under a reduced pressure of 3 mmHg at 120° C. to obtain 197.4 g of a transparent liquid compound.

The liquid compound had a viscosity of 15200 cSt at 25° C. and a refractive index of 1.334. From the measurement of $^1$H-NMR spectrum and IR absorption spectrum on the liquid compound, the following absorptions were observed.

| $^1$H-NMR( TMS standard) | $\delta$ = 3.42 ppm(S, N—CH$_3$, 12H) |
|---|---|
| | $\delta$ = 5.5–6.3 ppm(m, SiCH=CH$_2$, 6H) |
| | $\delta$ = 7.1–7.8 ppm(m, arom, 16H) |
| 1,100–1,300 cm$^{-1}$ | vC—F |
| 1,480, 1,580, 1,600 cm$^{-1}$ | varom |
| 1,690 cm$^{-1}$ | vC=O |

Further, from the determination of the amount of vinyl groups on this compound, it was found to be 0.014 mol/100 g. Thus, the obtained compound was confirmed to be an organosilicon compound represented by the following structural formula (18):

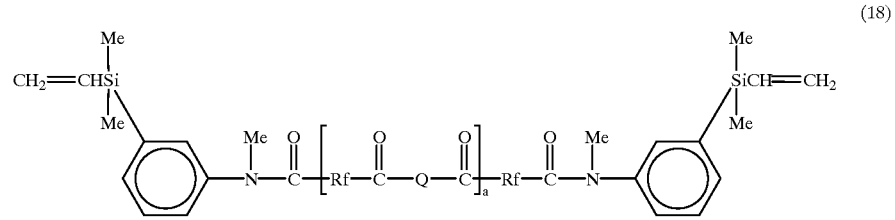

wherein Rf is a group represented by the following formula:

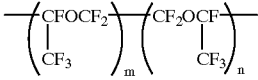

wherein m and n are an integer such that m+n is 38 on average, Q is a group represented by the following formula:

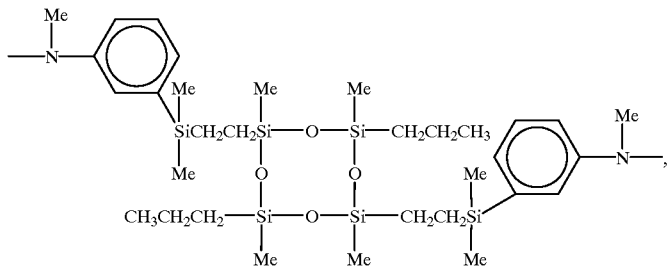

and a is 1 on average.

Production of a Fluorine-Containing Organosilicon Compound

Into a 500 ml four-necked flask provided with a stirring rod, a thermometer, a Dimroth condenser and a dropping funnel, 276.2 g of the compound having a vinyl group at both ends represented by said structural formula (18) and 55 g of m-xylene hexafluoride were charged, and they were heated to 80° C. on an oil bath while stirring. Then, 0.3 g of a 2% isopropylalcohol solution of chloroplatinic acid was added into the flask, followed by dropwise adding 7.3 g of trimethoxysilane thereto through the dropping funnel to effect a reaction. After the end of the addition, the reaction product was analyzed by NMR while aging, and it was confirmed that the vinyl groups (—CH=CH$_2$: δ=5.5–6.3 ppm) in the compound of the formula (18) had disappeared. Thereafter, stirring was effected under a reduced pressure of 10 mmHg at 100° C. to remove an unreacted silane component and to obtain 278.3 g of a pale yellowish, transparent liquid compound.

The obtained liquid compound had a viscosity of 34200 cSt at 25° C. and a refractive index of 1.338 at 25° C. From the measurement of $^1$H-NMR spectrum and IR absorption spectrum on the liquid compound, the following absorptions were observed.

| $^1$H-NMR( TMS standard) | δ = 3.67 ppm(S, Si—OCH$_3$, 18H) |
| | δ = 3.44 ppm(S, N—CH$_3$, 12H) |
| | δ = 7.1–7.8 ppm(m, arom, 16H) |
| IR | |
| 1,100–1,300 cm$^{-1}$ | νC—F |
| 1,480, 1,580, 1,600 cm$^{-1}$ | νarom |
| 1,690 cm$^{-1}$ | νC=O |

Further, the liquid compound was hydrolyzed to determine a released methanol, and the amount of the released methanol was found to be 0.044 mol/100 g. Thus, the liquid compound was confirmed to be a fluorine-containing organosilicon compound having the following structural formula (19):

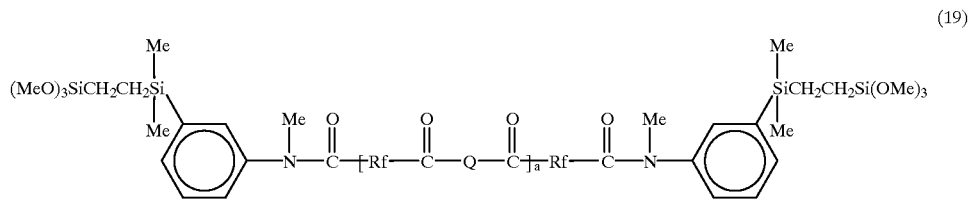

wherein Rf, Q and a are as defined in the formula (18).

Example 15

The same reaction and after-treatment as in the production of a fluorine-containing organosilicon compound in Example 14 were conducted to obtain 279.2 g of a pale yellowish, transparent liquid compound, except that 7.3 g of trimethoxysilane was replaced with 7.9 g of a silane compound represented by the following formula (20):

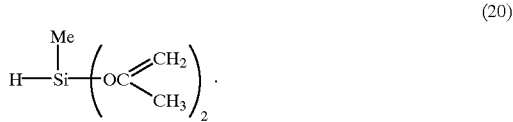

The obtained liquid compound had a viscosity of 35500 cSt at 25° C. and a refractive index of 1.340 at 25° C. From the measurement of $^1$H-NMR spectrum and IR absorption spectrum on the liquid compound, the following absorptions were observed.

| $^1$H-NMR( TMS standard) | δ = 3.40 ppm(S, N—CH$_3$, 12H) |
| | δ = 4.1–4.2 ppm(m, OC=CH$_2$, 8H) |
| | δ = 7.1–7.8 ppm(m, arom, 16H) |
| IR | |
| 1,100–1,300 cm$^{-1}$ | νC—F |
| 1,480, 1,580, 1,600 cm$^{-1}$ | νarom |
| 1,690 cm$^{-1}$ | νC=O |
| 1,645 cm$^{-1}$ | νC=C |

Further, the liquid compound was hydrolyzed to determine a released acetone, and the amount of the released acetone, it was found to be 0.028 mol/100 g. Thus, the liquid compound was confirmed to be a fluorine-containing organosilicon compound having the following structural formula (21):

(21)

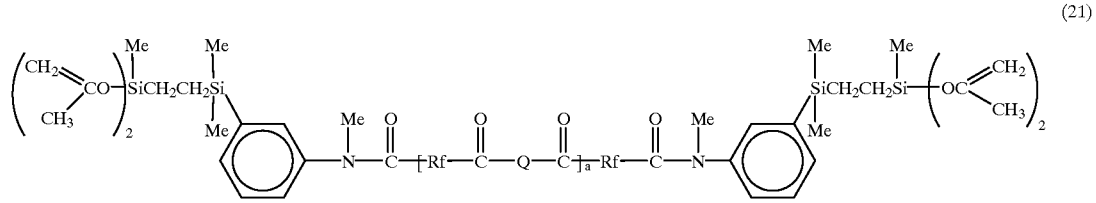

wherein Rf, Q and a are as defined in the formula (18).

Example 16

The same procedure as in Example 15 were conducted to obtain 280.1 g of a pale yellowish, transparent liquid compound, except that 7.9 g of the silane compound represented by said formula (20) was replaced with 8.1 g of a silane compound represented by the following formula (22):

(22)

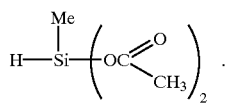

The obtained liquid compound had a viscosity of 35900 cSt at 25° C. and a refractive index of 1.341 at 25° C. From the measurement of $^1$H-NMR spectrum and IR absorption spectrum on the liquid compound, the following absorptions were observed.

| $^1$H-NMR( TMS standard) | $\delta$ = 1.94 ppm(S, SiOCCH$_3$, 12H) |
| | $\delta$ = 3.45 ppm(S, N—CH$_3$, 12H) |
| | $\delta$ = 7.1–7.8 ppm(m, arom, 16H) |
| IR | |
| 1,100–1,300 cm$^{-1}$ | vC—F |
| 1,480, 1,580, 1,600 cm$^{-1}$ | varom |
| 1,690 cm$^{-1}$ | vC=O (N—C=O) |
| 1,720 cm$^{-1}$ | vC=O (SiOC=O) |

Further, the liquid compound was hydrolyzed to determine a released acetic acid, and the amount of the released acetic acid was found to be 0.028 mol/100 g. Thus, the liquid compound was confirmed to be a fluorine-containing organosilicon compound having the following structural formula (23):

wherein Rf, Q and a are as defined in the formula (18).

Example 17

Into a 500 ml four-necked flask provided with a stirring rod, a thermometer, a Dimroth condenser and a dropping funnel, 393.9 g of a compound where in said formula (18), Rf is a group represented by the following formula:

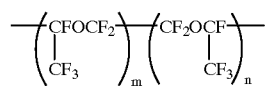

wherein m and n are an integer such that m+n is 38 on average, Q is a group represented by the following formula:

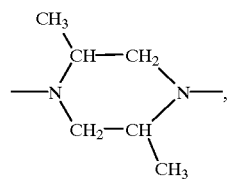

and n is 2 on average; and 64.8 g of m-xylene hexafluoride were charged, and they were heated to 70° C. on an oil bath while stirring. Then, 0.3 g of a 2% isopropylalcohol solution of chloroplatinic acid was added into the flask, followed by dropwise adding 7.3 g of trimethoxysilane thereto through the dropping funnel to effect a reaction. Thereafter, the same reaction and after-treatment as in the production of a fluorine-containing organosilicon compound in Example 14 were conducted to obtain 397.2 g of a pale yellowish, transparent liquid compound.

The obtained liquid compound had a viscosity of 84,700 cSt at 25° C. and a refractive index of 1.323 at 25° C. From the measurement of $^1$H-NMR spectrum and IR absorption spectrum on the liquid compound, the following absorptions were observed.

(23)

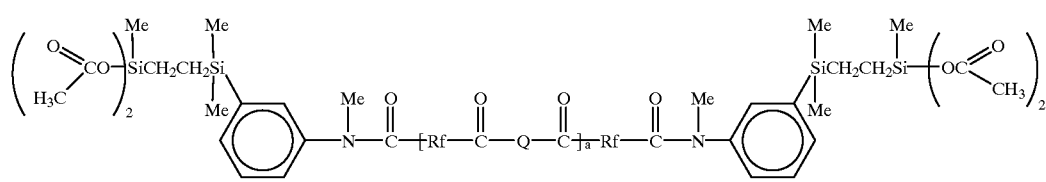

| $^1$H-NMR( TMS standard) | δ = 0.45 ppm(S, Si—CH$_3$, 12H) |
| --- | --- |
| | δ = 1.1–1.5 ppm(m, CH—CH$_3$, 12H) |
| | δ = 3.42 ppm(S, N—CH$_3$, 6H) |
| | δ = 3.63 ppm(S, SiO—CH$_3$, 18H) |
| | δ = 7.1–7.8 ppm(m, arom, 8H) |
| IR | |
| 1,100–1,300 cm$^{-1}$ | νC—F |
| 1,480, 1,560, 1,600 cm$^{-1}$ | νarom |
| 1,690 cm$^{-1}$ | νC=O |

Further, the liquid compound was hydrolyzed to determine a released methanol, and the amount of the released methanol was found to be 0.031 mol/100 g. Thus, the liquid compound was confirmed to be a fluorine-containing organosilicon compound having the following structural formula (24):

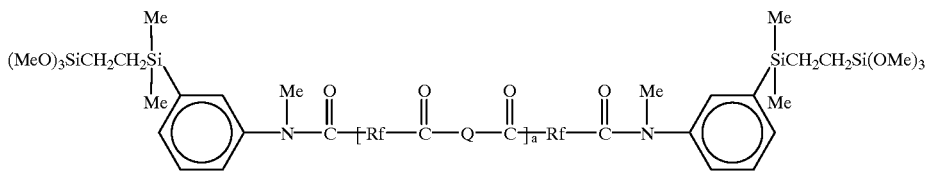

wherein Rf, Q and a are as defined in this Example.

Example 18

The same reaction and after-treatment as in the production of a fluorine-containing organosilicon compound in Example 14 were conducted to obtain 324.7 g of a pale yellowish, transparent liquid compound, except that 276.2 g of the compound having the formula (18) was replaced with 320.2 g of a compound represented by the following formula (25):

wherein m and n are an integer such that m+n is 94 on average, and the amount of m-xylene hexafluoride used was 60.0 g.

The obtained liquid compound had a viscosity of 18,700 cSt at 25° C. and a refractive index of 1.318 at 25° C. From the measurement of $^1$H-NMR spectrum and IR absorption spectrum on the liquid compound, the following absorptions were observed.

| $^1$H-NMR( TMS standard) | δ = 0.42 ppm(S, Si—CH$_3$, 12H) |
| --- | --- |
| | δ = 3.56 ppm(S, Si—OCH$_3$, 18H) |
| | δ = 7.1—7.8 ppm(m, arom, 8H) |
| IR | |
| 1,100–1,300 cm$^{-1}$ | νC—F |
| 1,540 cm$^{-1}$ | δN—H |
| 1,480, 1,580, 1,600 cm$^{-1}$ | νarom |
| 1,710 cm$^{-1}$ | νC=O |
| 3,330 cm$^{-1}$ | νN—H |

Further, the liquid compound was hydrolyzed to determine a released methanol, and the amount of the released methanol was found to be 0.038 mol/100 g. Thus, the liquid compound was confirmed to be a fluorine-containing organosilicon compound having the following structural formula (26):

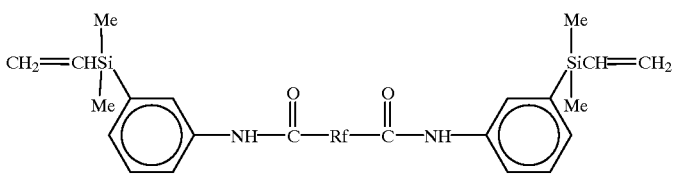

wherein Rf is a group represented by the following formula:

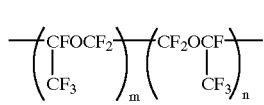

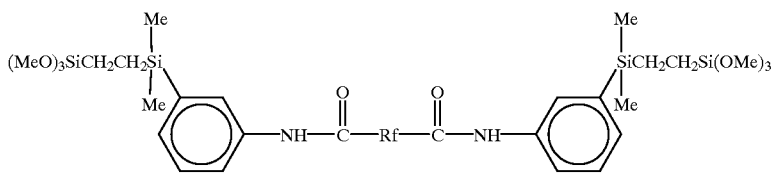

(26)

wherein Rf is as defined in the formula (25) of this Example.

Example 19
Preparation of a Third Room Temperature Curable Composition 100 g of the fluorine-containing organosilicon compound having the formula (19) obtained in Example 14 and 20 g of MT carbon were mixed and after the mixture was passed through a three-roll mill, it was mixed with 0.1 g of dibutyltin dioctoate to obtain composition I. The composition I was formed into a sheet having a thickness of 2 mm, and the sheet was left to stand and cured in an atmosphere of temperature: 20° C. and relative humidity: 55% for 14 days. The obtained sheet-like rubber elastomer (hereinafter, referred to as elastomer I) was measured for rubber physical properties in accordance with JIS C 2123. The results are shown in Table 4. Further, said composition I was stored in a sealed state at room temperature. The composition was stable for six months or more. From the composition I after six months, a sheet-like rubber elastomer (referred to as elastomer I') was prepared in the same manner as above and measured for rubber physical properties in the same manner as above. The results are shown in Table 4. Incidentally, hardness in the table is a value measured by a spring type hardness tester type A (the same being applied hereinafter).

TABLE 4

|  | Elastomer I | Elastomer II |
| --- | --- | --- |
| Hardness (JIS-A) | 39 | 38 |
| Tensile strength (kg/cm$^2$) | 25 | 26 |
| Elongation (%) | 250 | 260 |

Then, the elastomer I was evaluated for solvent resistance, resistance to acids and resistance to bases. The results are shown in Tables 6 and 7.

Solvent Resistance

A sample elastomer was dipped in each of solvents at 25° C. shown in Table 6 for 7 days to evaluate solvent-resistance from volume changes thereof. Incidentally, fluororubber in Table 6 is a Viton E-60C produced by E.I. Du Pont de Nemours and Company and used for comparison.

Resistance to Acids and Resistance to Bases

A sample elastomer was dipped in each of aqueous solutions at 25° C. shown in Table 7 for 7 days to evaluate resistance-to-acids and resistance-to-bases from volume changes thereof. Incidentally, the silicone rubber in Table 7 is a KE-951 produced by Shin-Etsu Chemical Co., Ltd. and used for comparison.

Example 20

The rubber physical properties of a rubber elastomer was measured in the same manner as in Example 19, except that the composition I was replaced with composition II which was prepared by mixing 100 g of the fluorine-containing organosilicon compound used in Example 19, 20 g of MT carbon, 2 g of fumed silica, 0.3 g of dibutyltin dilaurate, 2 g of vinyltrimethoxysilane and 1 g of γ-aminopropyltriethoxysilane. The results are shown in Table 5. Incidentally, in Table 5, elastomer II is a sheet-like elastomer obtained from the composition II immediately after prepared and elastomer II' is a sheet-like elastomer obtained from the composition II stored in a sealed state at room temperature for six months.

The elastomer II was evaluated for solvent resistance, resistance to acids and resistance to bases in the same manner as in Example 19. The results are shown in Tables 6 and 7. Additionally, the elastomer II obtained in this Example was evaluated for heat resistance and cold resistance as follows. The resuls are shown in Tables 8 and 9.

Heat Resistance

The elastomer II was measured and evaluated for rubber physical properties before and after being heated at 250° C. 120 hours in accordance with JIS C 2123. Incidentally, Table 8 listed also an decrease (decrease of weight by heating: weight %) of the weight after heated, based on the weight before heated.

Cold Resistance

A specimen was cooled at −70° C. in a mixture of dry ice and ethanol and then heated up at a rate of 1° C. per minute. At that time, rigidity at each temperature was measured by a Gehman torsion tester manufactured by Ueshima Seisakusho, and the temperatures when the rigidity reached two times, five times, ten times and hundred times the rigidity at room temperature were represented as $T_2$, $T_5$, $T_{10}$ and $T_{100}$, respectively. Incidentally, the fluororubber shown in Table 9 is a Viton E-60C produced by E.I. Du Pont de Nemours and Company and used for comparison.

TABLE 5

|  | Elastomer II | Elastomer II' |
| --- | --- | --- |
| Hardness (JIS-A) | 37 | 38 |
| Tensile strength (kg/cm$^2$) | 24 | 25 |
| Elongation (%) | 230 | 220 |

TABLE 6

|  | Volume Change (%) | | |
| --- | --- | --- | --- |
|  | Elastomer I | Elastomer II | Fluororubber |
| Toluen | 8 | 9 | 22 |
| n-Hexane | 7 | 7 | 1 |

TABLE 6-continued

| | Volume Change (%) | | |
|---|---|---|---|
| | Elastomer I | Elastomer II | Fluororubber |
| Methanol | 3 | 3 | 90 |
| Methyl ethyl hexane | 5 | 8 | 240 |

TABLE 7

| | Volume Change (%) | | |
|---|---|---|---|
| | Elastomer I | Elastomer II | Silicone rubber |
| 10% Aqueous solution of NaOH | 0 | 0 | 0 |
| 10% Aqueous solution of HCl | 0 | 0 | 2 |
| 10% Aqueous solution of nitric acid | 0 | 1 | 8 |
| 10% Aqueous solution of sulfuric acid | 0 | 1 | 5 |

TABLE 8

| | Before heated | After heated |
|---|---|---|
| Hardness (JIS-A) | 39 | 38 |
| Elongation (%) | 250 | 220 |
| Tensile strength (kg/cm$^2$) | 25 | 24 |
| Decrease of weight by heating | — | 0.4 |

TABLE 9

| | Elastomer II | Fluororubber |
|---|---|---|
| T$_2$ | −35° C. | −7° C. |
| T$_5$ | −48° C. | −11° C. |
| T$_{10}$ | −51° C. | −13° C. |
| T$_{100}$ | −55° C. | −19° C. |

Example 21

A mixture of 100 parts by weight of the fluorine-containing organosilicon compound used in Example 19 and 2 parts by weight of methyltrimethoxysilane was dissolved in m-xylene hexafluoride to prepare a 20 weight % solution of said mixture. A slide glass was dipped in the solution for 30 seconds and left to stand under the condition of 20° C. and 55% RH for 18 hours to form a cured film on the surface thereof. On the slide glass on which surface the cured film had been formed, each of a droplet of n-hexadecane and a droplet of pure water was laid to measure a contact angle of each droplet with the slide glass. The results are shown in Table 10.

Example 22

A mixture of 100 parts by weight of the fluorine-containing organosilicon compound used in Example 19, 2 parts by weight of methyltrimethoxysilane and 0.2 part by weight of dibutyltin dilaurate was dissolved in m-xylene hexafluoride to prepare a 50 weight % solution of said mixture. After the solution was applied to the surface of a slide glass, the slide glass was left to stand under the condition of 20° C. and 55% RH for 6 hours to form a cured film on the surface thereof. The slide glass on which surface the cured film had been formed was measured for the contact angle similarly to Example 21. The results are shown in Table 10.

TABLE 10

| | Contact Angle (degree) | |
|---|---|---|
| | Pure water | n-Hexadecane |
| Example 21 | 118 | 71 |
| Example 22 | 117 | 70 |

What is claimed is:

1. A room temperature curable fluoropolymer composition, comprising:

(A) a straight chain fluoropolymer compound containing, in a backbone chain thereof, at least one structure selected from the group consisting of a perfluoroalkylene structure and a perfluoropolyether structure and having a hydrolyzable silyl group at both ends of a molecular chain thereof;

(B') an organosilicon compound having at least two silanol groups per molecule; and (C') a condensation accelerator;

wherein the amount of component (B') is 0.01 to 200 parts by weight per 100 parts by weight of a component (A), and the amount of component (C') is 0.01 to 5 parts by weight per 100 parts by weight of the total amount of component (A) and component (B').

2. The composition of claim 1, wherein the straight chain fluoropolymer compound of component (A) has the formula (1):

$$Y—[R^1—(Rf—R^2)_a—Rf—R^1]—Y \qquad (1)$$

wherein Rf is at least one divalent group selected from the group consisting of perfluoroalkylene and divalent perfluoropolyether; R$^1$ and R$^2$, which are the same or different, are each an optionally substituted divalent hydrocarbon group which optionally contains at least one atom selected from the group consisting of oxygen, nitrogen and silicon; a is an integer of 0 or more; and Y is a hydrolyzable silyl group.

3. The composition of claim 1, wherein the straight chain fluoropolymer compound of component (A) has a viscosity of 25 to 1,000,000 cSt at 25° C.

4. The composition of claim 1, wherein component (B') is at least one compound selected from the group consisting of a compound having the formula (6):

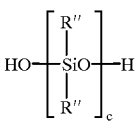

$$(6)$$

wherein c is an integer of 1 or more, and R" is an optionally substituted monovalent hydrocarbon group having 1 to 8 carbon atoms; and a compound having the formula (7):

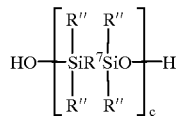 (7)

wherein $R^7$ is an optionally substituted divalent hydrocarbon group having 1 to 20 carbon atoms, and c and R" are as defined in the formula (6).

5. The composition of claim 1, wherein component (C') is at least one compound selected from the group consisting of amine salts and metal salts of organic carboxylic acids, organic acids, organotitanium compounds, amine compounds and salts thereof, quaternary ammonium salts, alkali metal salts of low aliphatic acids, dialkylhydroxyl amines, and guanidyl-containing compounds.

6. The composition of claim 3, wherein the straight chain fluoropolymer compound of component (A) has a viscosity of 100 to 100,000 cSt at 25° C.

7. The composition of claim 4, wherein in both the formula (6) and (7), c is an integer of 1 to 200.

8. The composition of claim 4, wherein in the formula (7), $R^7$ is an optionally substituted divalent hydrocarbon group of 2 to 10 carbon atoms.

9. The composition of claim 1, wherein component (A), said straight chain fluoropolymer compound has, in the backbone chain thereof, at least one perfluoroalkylene structure of the formula (2):

$$-C_pF_{2p}- \qquad (2)$$

wherein p is an integer of 1 to 10.

10. The composition of claim 9, wherein in the formula (2), p is an integer of 1 to 6.

11. The composition of claim 1, wherein in component (A), said straight chain fluoropolymer compound has, in the backbone chain thereof, at least one perfluoropolyether structure of the formula (3):

$$-(Rf-O)_q \qquad (3)$$

wherein a plurality of Rf, which are the same or different, are a straight chain or branched chain perfluoroalkylene group having 1 to 6 carbon atoms; and q is a integer of 1 to 500.

12. The composition of claim 11, wherein in the formula (3), a plurality of Rf, which are the same or different, are a straight chain or branched chain perfluoroalkylene group having 1 to 3 carbon atoms; and q is an integer of 2 to 400.

13. The composition of claim 12, wherein q is an integer of 10 to 200.

14. A cured product obtained by curing the composition of claim 1.

* * * * *